US012807864B2

(12) United States Patent
Sokol et al.

(10) Patent No.: US 12,807,864 B2
(45) Date of Patent: Nov. 24, 2026

(54) ELECTROCHROMIC DEVICES AND COMPOSITIONS INCLUDING CATHODIC ZWITTERIONS

(71) Applicant: Vitro Flat Glass LLC, Cheswick, PA (US)

(72) Inventors: Ivan Alexandrovich Sokol, Pittsburgh, PA (US); Dylan Thomas Christiansen, Pittsburgh, PA (US)

(73) Assignee: Vitro Flat Glass LLC, Cheswick, PA (US)

( * ) Notice: Subject to any disclaimer, the term of this patent is extended or adjusted under 35 U.S.C. 154(b) by 758 days.

(21) Appl. No.: 18/130,932

(22) Filed: Apr. 5, 2023

(65) Prior Publication Data

US 2023/0340319 A1 Oct. 26, 2023

Related U.S. Application Data

(60) Provisional application No. 63/333,234, filed on Apr. 21, 2022.

(51) Int. Cl.
*C09K 9/00* (2006.01)
*C07C 311/48* (2006.01)
(Continued)

(52) U.S. Cl.
CPC .............. *C09K 9/02* (2013.01); *C07C 311/48* (2013.01); *C07D 213/53* (2013.01);
(Continued)

(58) Field of Classification Search
CPC .............. C09K 9/02; C09K 2211/1018; C09K 2211/1466; G02F 1/15165; G02F 1/13439;
(Continued)

(56) References Cited

U.S. PATENT DOCUMENTS 6,372,159 B1 4/2002 Berneth et al.
6,545,793 B2 4/2003 Berneth et al.
(Continued)

FOREIGN PATENT DOCUMENTS

CN 107438793 A 12/2017
DE 102009024207 A1 * 1/2010 .......... G02F 1/1525
(Continued)

OTHER PUBLICATIONS

Bhandari et al., "A Dual Electrochrome of Poly-(3,4-Ethylenedioxythiophene) Doped by N, N'-Bis(3-sulfonatopropyl)-4-4'-bipyridinium—Redox Chemistry and Electrochromism in Flexible Devices", ChemSusChem, 2010, pp. 97-105, vol. 3, No. 1.
(Continued)

*Primary Examiner* — James E Mcdonough
(74) *Attorney, Agent, or Firm* — The Webb Law Firm

(57) ABSTRACT

The present invention relates to electrochromic devices and compositions, which include a cathodic component that includes cathodic zwitterions, where an anion is covalently bonded by a divalent linking group to a pyridinium nitrogen of the cathodic component. Each covalently bonded anion is independently represented by the following Formula (III) or Formula (IV):

(III)

$—R^6—SO_3^-$, or (IV)

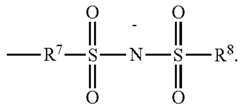

With reference to Formula (III) and Formula (IV), $R^6$ and $R^7$ are in each case independently selected from divalent linear
(Continued)

or branched alkane linking group, and for Formula (IV), $R^8$ is selected from fluorine, linear or branched fluorinated alkyl, or linear or branched perfluorinated alkyl.

23 Claims, 2 Drawing Sheets

(51) Int. Cl.

| | |
|---|---|
| ***C07D 213/53*** | (2006.01) |
| ***C07D 279/22*** | (2006.01) |
| ***C08F 36/02*** | (2006.01) |
| ***C09K 9/02*** | (2006.01) |
| ***G02F 1/1343*** | (2006.01) |
| ***G02F 1/1516*** | (2019.01) |
| ***G02F 1/155*** | (2006.01) |
| *G02F 1/1514* | (2019.01) |

(52) U.S. Cl.

CPC ............ *C07D 279/22* (2013.01); *C08F 36/02* (2013.01); *G02F 1/13439* (2013.01); *G02F 1/15165* (2019.01); *G02F 1/155* (2013.01); *C09K 2211/1018* (2013.01); *C09K 2211/1466* (2013.01); *G02F 2001/15145* (2019.01)

(58) Field of Classification Search

CPC ........... G02F 1/155; G02F 2001/15145; C07C 311/48; C07D 213/53; C08F 36/02

USPC ........................................................ 106/31.16

See application file for complete search history.

(56) References Cited

U.S. PATENT DOCUMENTS

| | | | |
|---|---|---|---|
| 7,595,011 B2 | 9/2009 | Kanouni et al. | |
| 7,718,096 B2 | 5/2010 | Yale et al. | |
| 8,867,116 B1 | 10/2014 | Kloeppner et al. | |
| 2002/0145790 A1 | 10/2002 | Berneth | |
| 2016/0377946 A1 | 12/2016 | Baumann et al. | |
| 2017/0146880 A1 | 5/2017 | Baumann et al. | |
| 2021/0313569 A1 * | 10/2021 | Choi | H01M 4/36 |

FOREIGN PATENT DOCUMENTS

| | | | |
|---|---|---|---|
| WO | 2016209323 A1 | 12/2016 | |
| WO | WO-2017087019 A1 * | 5/2017 | C09K 11/06 |

OTHER PUBLICATIONS

Kevan et al., "Applications of electron spin echo spectroscopy to location control of alkylphenothiazine derivatives in photoinduced charge separation across vesicles, micelles and reverse micelle interfaces" International Journal of Radiation Applications and Instrumentation, Part C: Radiation Physics and Chemistry, 1992, pp. 333-344, vol. 39, No. 4.

Sen et al., "Viologens as Charge Carriers in a Polymer-Based Battery Anode", Applied Materials & Interfaces, 2013, pp. 7825-7830, vol. 5, No. 16.

Wang et al., "Preparation and characterization of gel polymer electrolytes using poly(ionic liquids) and high lithium salt concentration ionic liquids", Journal of Materials Chemistry A, 2017, Abstract, vol. 5, No. 45.

* cited by examiner

ELECTROCHROMIC DEVICES AND COMPOSITIONS INCLUDING CATHODIC ZWITTERIONS

CROSS-REFERENCE TO RELATED APPLICATION

This application is entitled to and claims priority to U.S. Provisional Patent Application No. 63/333,234, filed on Apr. 21, 2022, the disclosure of which is incorporated herein by reference in its entirety.

FIELD

The present invention relates to electrochromic devices and compositions that include a cathodic component that includes cathodic zwitterions, where an anion is covalently bonded by a divalent linking group to a pyridinium nitrogen of the cathodic component.

BACKGROUND

Electrochromism involves a reversible change in a material's visible color and/or transmittance of visible light with the application of an electrical potential. The change in color and/or transmittance typically involves alternately cycled oxidized and reduced charge states. Generally, a material that generates a color while undergoing reduction is referred to as a cathodically-coloring electrochromic material; and a material that generates color while undergoing oxidation is referred to as an anodically-coloring electrochromic material.

Electrochromic devices typically include opposed electrodes (e.g., an anode and a cathode) having interposed there-between an electrochromic layer that is solution or gel-based. The kinetics of such electrochromic devices is typically governed primarily by mass transport of cathodic components and anodic components across and through the electrochromic layer. With some electrochromic systems, the cathodic component is positively charged, and the anodic component is neutral or non-charged. With such systems, the positively charged cathodic component is typically transported at a higher rate across the electrochromic layer towards the cathode, than is the non-charged anodic component as it diffuses towards the anode. Such a transport imbalance can result in undesirably increased overpotentials at the anodic interface and correspondingly overoxidation. Overoxidation can undesirably result in reduced durability of the electrochromic device.

It would be desirable to develop new electrochromic devices and compositions in which the active components thereof, and in particular, the cathodic and anodic components, provide improved mass transport balance. It would be further desirable that such newly developed electrochromic devices and compositions provide, or otherwise have associated therewith, improved durability, reduced costs of manufacture and/or operation, and/or improved efficiency of operation.

SUMMARY

In accordance with the present invention, there is provided an electrochromic device comprising: (a) a first substrate having a surface comprising a first transparent electrode layer; (b) a second substrate having a surface comprising a second transparent conductive electrode layer, wherein the first transparent electrode layer and the second transparent electrode layer are in opposing spaced opposition; and (c) an electrochromic layer interposed between the first transparent electrically conductive electrode layer and the second transparent electrically conductive electrode layer. The electrochromic layer comprises: (i) a cathodic component; (ii) an anodic component; (iii) an optional electrolyte; and (iv) a polymer matrix. The cathodic component comprises a cathodic component having cationic charge selected from at least one of a 1,1'-disubstituted-4,4'-dipyridinium cation represented by the following Formula (I), or a 1,1-(alkane-alpha, omega-diyl)-bis-(1'-substituted-4,4'-dipyridinium) cation represented by the following Formula (II),

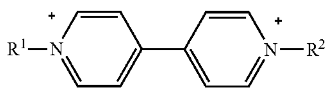

(I)

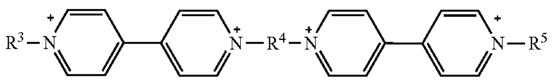

(II)

With reference to Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by the following Formula (III), $$R^6—SO_3^- \quad \text{(III), and}$$

a group represented by the following Formula (IV),

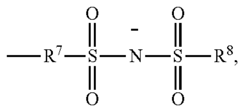

(IV)

With reference to Formula (III) and Formula (IV), $R^6$ and $R^7$ are in each case independently selected from divalent linear or branched alkane linking group, and for Formula (IV), $R^8$ is selected from fluorine, linear or branched fluorinated alkyl, or linear or branched perfluorinated alkyl. With further reference to Formula (II), $R^4$ is selected from divalent linear or branched alkane linking group. There is provided, that for Formula (I), at least one of $R^1$ and $R^2$ is independently selected from the group represented by Formula (III) or the group represented by Formula (IV). There is also provided that for Formula (II), at least one of $R^3$ and $R^5$ is independently selected from the group represented by Formula (III) or the group represented by Formula (IV).

In accordance with the present invention, there is further provided an electrochromic composition comprising: (i) a cathodic component; (ii) an anodic component; (iii) an optional electrolyte; (iv) a polymeric thickener; and (v) a solvent. The cathodic component, of the electrochromic composition, comprises a cathodic component having cationic charge selected from at least one of a 1,1'-disubstituted-4,4'-dipyridinium cation represented by Formula (I) as provided above, or a 1,1-(alkane-alpha, omega-diyl)-bis-(1'-substituted-4,4'-dipyridinium) cation represented by Formula (II) as provided above. With Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by Formula (III) as provided above, and a group represented by Formula (IV) as provided above. With Formula (III) and Formula (IV), $R^6$ and $R^7$ are in each case independently selected from divalent linear or branched alkane linking group. With Formula (IV), $R^8$ is selected from fluorine, linear or branched fluorinated alkyl, or linear or branched perfluorinated alkyl. For Formula (II), $R^4$ is selected from divalent linear or branched alkane linking group. There is provided, that for Formula (I), at least one of $R^1$ and $R^2$ is independently selected from the group represented by Formula (III) or the group represented by Formula (IV). There is also provided that for Formula (II), at least one of $R^3$ and $R^5$ is independently selected from the group represented by Formula (III) or the group represented by Formula (IV).

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 and 2 like characters refer to the same components and/or elements, as the case may be, unless otherwise stated.

DETAILED DESCRIPTION

Figure 1:
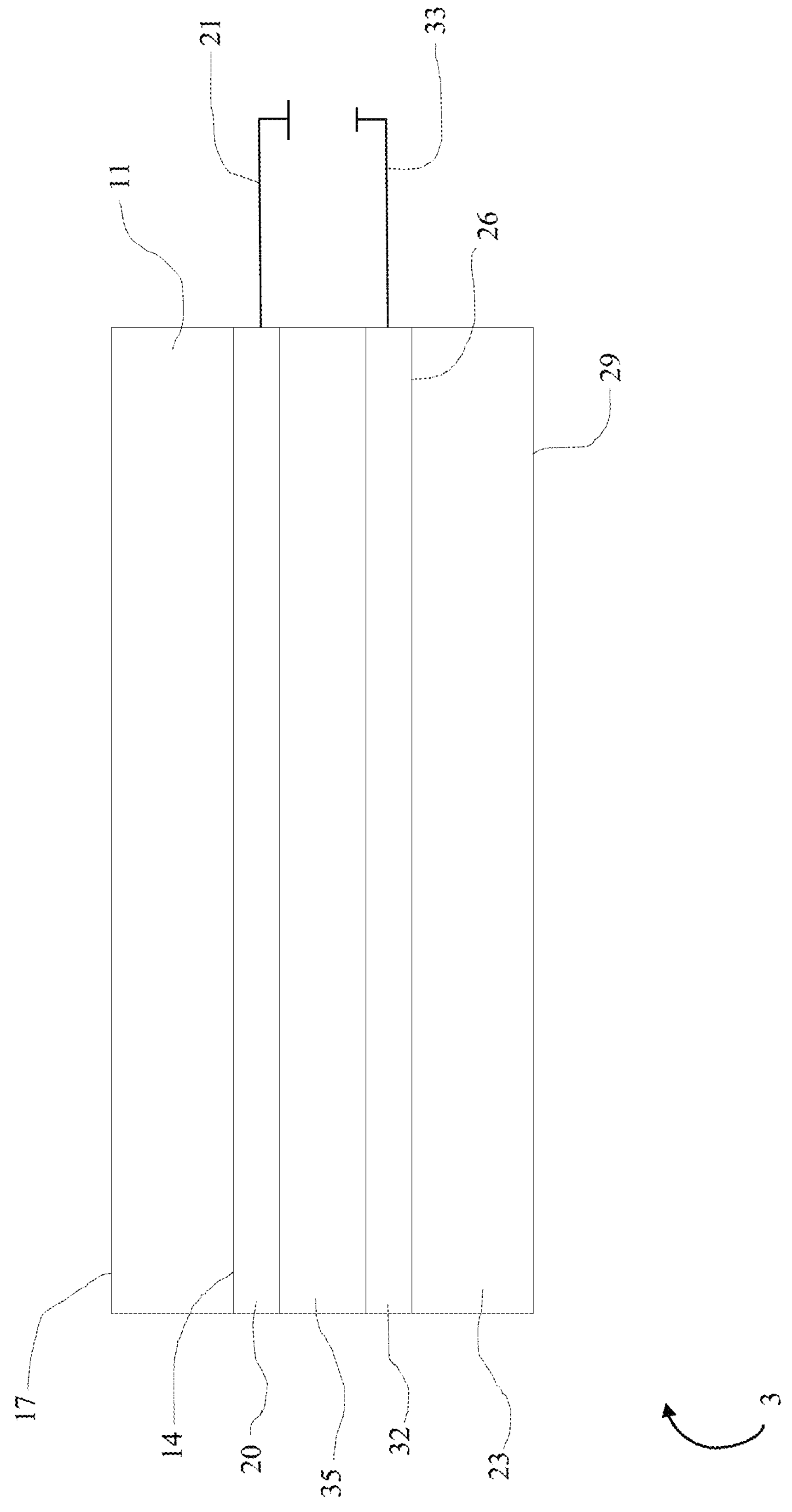
FIG. 1 is a representative side elevational sectional view of an electrochromic device according to the present invention.

As used herein, the articles "a," "an," and "the" include plural referents unless otherwise expressly and unequivocally limited to one referent.

Unless otherwise indicated, all ranges or ratios disclosed herein are to be understood to encompass any and all values, and subranges or subratios subsumed therein. For example, a stated range or ratio of "1 to 10" should be considered to include any and all values there-between (such as, 1, 2, 3, 4, 5, 6, 7, 8, 9, and 10), and subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

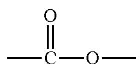

or equivalently —C(O)O—, is inclusive of the right-to-left representation thereof,

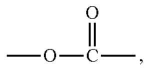

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth) acrylic acid" means methacrylic acid and/or acrylic acid.

As used herein, the term "electrochromic" and similar terms, such as "electrochromic compound" means having an absorption spectrum for at least visible radiation that varies in response to the application of an electric potential. Further, as used herein the term "electrochromic material" means any substance that is adapted to display electrochromic properties (such as, adapted to have an absorption spectrum for at least visible radiation that varies in response to an applied electric potential) and which includes at least one electrochromic compound.

As used herein, the term "electric potential" and related terms such as "electrical potential" means an electric potential that is capable of causing a response in a material, such as, but not limited to, transforming an electrochromic material from one form or state to another, as will be discussed in further detail herein.

As used herein to modify the term "state," the terms "first" and "second" are not intended to refer to any particular order or chronology, but instead refer to two different conditions or properties. For purposes of non-limiting illustration, the first state and the second state of an electrochromic compound, such as an anodically-coloring electrochromic compound, can differ with respect to at least one optical property, such as but not limited to the absorption of visible and/or UV radiation. Thus, according to various non-limiting embodiments disclosed herein, the anodically-coloring electrochromic compounds of the present invention can have a different absorption spectrum in each of the first and second state. For example, while not limiting herein, an anodically-coloring electrochromic compound can be clear in the first state and colored in the second state. Alternatively, an anodically-coloring electrochromic compound can have a first color in the first state and a second color in the second state.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation there-through. Non-limiting examples of windows include automotive and aircraft transparencies, windshields, filters, shutters, and optical switches.

As used herein the term "mirror" means a surface that specularly reflects a large fraction of incident light.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the terms "interposed" and "interposed between," mean residing or positioned between, but not necessarily in direct (or abutting) contact with overlying and/or underlying elements, or surfaces thereof. For example, a layer "interposed between" a first substrate and a second substrate does not preclude the presence of one or more other layers, coatings, or films of the same or different composition located between the interposed layer and the first and/or second substrates.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_3$-$C_{10}$ alkyl, or cyclic $C_5$-$C_7$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_2$-$C_{10}$ heterocycloalkyl groups, such as $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The descriptions, classes, and examples provided herein with regard to alkyl groups, cycloalkyl groups, heterocycloalkyl groups, haloalkyl groups, and the like, are also applicable to alkane groups, cycloalkane groups, heterocycloalkane groups, haloalkane groups, etc., such as, but not limited to, polyvalent alkane groups, such as polyvalent alkane linking groups, such as divalent alkane linking groups.

As used herein, the term "aryl" and related terms, such as "aryl group", means an aromatic cyclic monovalent hydrocarbon radical. As used herein, the term "aromatic" and related terms, such as "aromatic group," means a cyclic conjugated hydrocarbon having stability (due to delocalization of pi-electrons) that is significantly greater than that of a hypothetical localized structure. Examples of aryl groups include $C_6$-$C_{14}$ aryl groups, such as, but not limited to, phenyl, naphthyl, phenanthryl, and anthracenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, quinolinyl, isoquinolinyl, and pyrimidinyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl, and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl.

The term "nitrogen-containing heterocycle," such as "nitrogen-containing heterocycle group" or nitrogen-containing heterocycle substituent," as used herein, includes, but is not limited to, a nitrogen-containing ring in which the nitrogen-containing ring is bonded through a ring nitrogen. Examples of nitrogen-containing heterocycles include, but are not limited to, aliphatic cyclic aminos (or cycloaliphatic aminos), such as morpholino, piperidino, pyrrolidino, and decahydroisoquinolino; and heteroaromatics, such as imidazole, pyrrole, indole, and carbazole.

As used herein, recitations of "substituted" group, means a group including, but not limited to, alkyl group, cycloalkyl group, heterocycloalkyl group, aryl group, and/or heteroaryl group, in which at least one hydrogen thereof has been replaced or substituted with a group or "substituent" that is other than hydrogen, such as, but not limited to: alkoxy groups; halo groups (e.g., F, Cl, I, and Br); hydroxyl groups; thiol groups; alkylthio groups; arylthio groups; ketone groups; aldehyde groups; carboxylic ester groups; carboxylic acid groups; phosphoric acid groups; phosphoric acid ester groups; sulfonic acid groups; sulfonic acid ester groups; nitro groups; cyano groups; alkyl groups; alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); aralkyl groups; heteroaryl groups (including poly-fused-ring heteroaryl groups); amino groups, such as —$N(R^{11'})(R^{12'})$ where $R^{11'}$ and $R^{12'}$ are each independently selected from, for example, hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; trialkylsilyl groups; nitrogen-containing heterocycles; or combinations thereof, including those classes and examples as described further herein. In accordance with some embodiments of the present invention, the substituents of a substituted group are more particularly recited.

As used herein, the term "halo" and related terms, such as "halo group," "halo substituent," "halogen group," and "halogen substituent," means a single bonded halogen group, such as —F, —Cl, —Br, and —I.

As used herein, recitations of "halo substituted" and related terms (such as, but not limited to, haloalkyl groups, haloalkenyl groups, haloalkynyl groups, haloaryl groups, and halo-heteroaryl groups) means a group in which at least one, and up to and including all of the available hydrogen groups thereof is substituted with a halo group, such as, but not limited to F, Cl or Br. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For purposes of non-limiting illustration: perhalomethyl is —$CX_3$; and perhalophenyl is —$C_6X_5$, where X represents one or more halo groups, such as, but not limited to F, Cl, Br, or I.

As used herein, "at least one of" is synonymous with "one or more of," whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the present invention herein may describe certain features as being "particularly" or "preferably" within certain limitations (e.g., "preferably," "more preferably," or "even more preferably," within certain limitations). It is to be understood that the invention is not limited to or by such particular or preferred limitations, but encompasses the entire scope of the disclosure.

As used herein, and in accordance with some embodiments, the term "ketone" such as with regard to groups, and substituents of various groups, of the compounds and components of the present invention, and related terms, such as "ketone group" and "ketone substituent," includes a material represented by —C(O)R, where R is selected from those groups as described below, other than hydrogen.

As used herein, and in accordance with some embodiments, the term "carboxylic acid" such as with regard to groups, and substituents of various groups, of the compounds and components of the present invention, and related terms, such as "carboxylic acid group" and "carboxylic acid substituent" includes a material represented by —C(O)OH.

As used herein, and in accordance with some embodiments, the term "ester" such as with regard to groups, and substituents of various groups, of the compounds and components of the present invention, and related terms, such as "ester group" and "ester substituent" means a carboxylic acid ester group represented by —C(O)OR, where R is selected from those groups as described below, other than hydrogen.

As used herein, and in accordance with some embodiments, the term "carboxylate" such as with regard to groups, and substituents of various groups, of the compounds and components of the present invention, and related terms, such as "carboxylate group" and "carboxylate substituent," includes a material represented by —OC(O)R, where R is selected from those groups as described below.

As used herein, and in accordance with some embodiments, the term "amide" such as with regard to groups, and substituents of various groups, of the compounds and components of the present invention, and related terms, such as "amide group" and "amide substituent" includes a material represented by —C(O)N(R)(R) or —N(R)C(O)R, where each R is independently selected from those groups as described below.

As used herein, and in accordance with some embodiments, the term "carbonate" such as with regard to groups, and substituents of various groups, of the compounds and components of the present invention, and related terms, such as "carbonate group" and "carbonate substituent" includes a material represented by —OC(O)OR, where R is selected from those groups as described below, other than hydrogen.

As used herein, and in accordance with some embodiments, the term "carbamate" such as with regard to groups, and substituents of various groups, of the compounds and components of the present invention, and related terms, such as "carbamate group" and "carbamate substituent" includes a material represented by —OC(O)N(R)(H) or —N(H)C(O)OR, where R in each case is independently selected from those groups as described below, other than hydrogen.

As used herein, and in accordance with some embodiments, the term "urea" such as with regard to groups, and substituents of various groups, of the compounds and components of the present invention, and related terms, such as "urea group" and "urea substituent" includes a material represented by —N(R)C(O)N(R)(R), where each R is independently selected from those groups as described below.

As used herein, and in accordance with some embodiments, the term "siloxy" such as with regard to groups, and substituents of various groups, of the compounds and components of the present invention, and related terms, such as "siloxy group" and "siloxy substituent" includes a material represented by —O—$Si(R)_3$ where each R is independently selected from those groups as described below, other than hydrogen.

As used herein, and in accordance with some embodiments, the term "alkoxysilane" such as with regard to groups, and substituents of various groups, of the compounds and components of the present invention, and related terms, such as "alkoxysilane group" and alkoxysilane substituent" includes a material represented by —$Si(OR'')_w(R)_t$, where w is 1 to 3 and t is 0 to 2, provided the sum of w and t is 3; R" for each w is independently selected from alkyl; and R for each t is independently selected from those groups as described below, other than hydrogen.

As used herein, and in accordance with some embodiments, the term "polysiloxane" such as with regard to groups, and substituents of various groups, of the compounds and components of the present invention, and related terms, such as "polysiloxane group" and "polysiloxane substituent", includes a material represented by the following Formula (B):

(B)

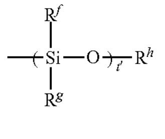

With reference to Formula (A): t' is greater than or equal to 2, such as from 2 to 200; $R^f$ and $R^g$ for each t' are each independently selected from a group R as described below, other than hydrogen; and $R^h$ is independently a group R as described below.

Unless otherwise stated, each R group of each of the above described ketone, ester (carboxylic acid ester), carboxylate, amide, carbonate, carbamate, urea, siloxane, alkoxysilane groups, and polysiloxane groups, is in each case independently selected from hydrogen, alkyl, haloalkyl, perhaloalkyl, cycloalkyl, heterocycloalkyl, aryl, heteroaryl, and combinations thereof (including those classes and examples thereof as recited previously herein).

In accordance with the present invention, the electrochromic material (of the electrochromic layer of the electrochromic device) includes a cathodic material having cationic charge selected from at least one of a 1,1'-disubstituted-4,4'-dipyridinium cation represented by Formula (I) as described previously herein, and/or a 1,1-(alkane-alpha,omega-diyl)-bis-(1'-substituted-4,4'-dipyridinium) cation represented by Formula (II) as described previously herein.

The aryl groups of the unsubstituted aryl groups and substituted aryl groups, from which $R^1$ and $R^2$ of Formula (I), and $R^3$ and $R^5$ of Formula (II), can each be independently selected, include those aryl groups as recited previously herein, such as, but not limited to, phenyl, naphthyl, phenanthryl, and anthracenyl. The cycloalkyl groups of the unsubstituted cycloalkyl groups and substituted cycloalkyl groups, from which $R^1$ and $R^2$ of Formula (I), and $R^3$ and $R^5$ of Formula (II), can each be independently selected, include those cycloalkyl groups as recited previously herein, such as, but not limited to, cyclopentyl, cyclohexyl, and cycloheptyl.

The substituents of the substituted cycloalkyl and substituted aryl groups, from which $R^1$ and $R^2$ of Formula (I), and $R^3$ and $R^5$ of Formula (II), can each be independently selected, include those substituents as recited previously herein. With some embodiments, each substituent of the substituted cycloalkyl and substituted aryl groups, from which $R^1$ and $R^2$ of Formula (I), and $R^3$ and $R^5$ of Formula (II), can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; heterocycloalkyl groups; aryl groups; aralkyl groups (such as, benzyl groups); heteroaryl groups; and amino groups.

The linear or branched alkyl groups from which $R^1$ and $R^2$ of Formula (I), and from which $R^3$ and $R^5$ of Formula (II), can each be independently selected, include those classes and examples of alkyl groups as recited previously herein, such as, but not limited to, methyl, ethyl, linear or branched propyl, linear or branched butyl, linear or branched pentyl, linear or branched hexyl, and linear or branched heptyl.

In accordance with some embodiments and with reference to Formula (I) and Formula (II), $R^1$, $R^2$, $R^3$, and $R^5$ are in each case independently selected from linear or branched $C_1$-$C_{10}$ alkyl (or linear or branched $C_1$-$C_8$ alkyl, or linear or branched $C_1$-$C_4$ alkyl), unsubstituted $C_3$-$C_7$ cycloalkyl, substituted $C_3$-$C_7$ cycloalkyl, unsubstituted phenyl, substituted phenyl, the anion group represented by Formula (III), and the anion group represented by Formula (IV). With reference to Formula (III) and Formula (IV), and in accordance with some embodiments, $R^6$ and $R^7$ are in each case independently selected from divalent linear or branched $C_1$-$C_{10}$ alkane linking group (or divalent linear or branched $C_1$-$C_8$ alkane linking group, or divalent linear or branched $C_1$-$C_4$ alkane linking group). With reference to Formula (IV), and with some embodiments, $R^8$ is selected from fluorine, linear or branched fluorinated $C_1$-$C_{10}$ alkyl (or linear or branched fluorinated $C_1$-$C_8$ alkyl, or linear or branched fluorinated $C_1$-$C_4$ alkyl), or linear or branched perfluorinated $C_1$-$C_{10}$ alkyl (or linear or branched perfluorinated $C_1$-$C_8$ alkyl, or linear or branched perfluorinated $C_1$-$C_4$ alkyl). In accordance with some embodiments, and with reference to Formula (II), $R^4$ is selected from divalent linear or branched $C_1$-$C_{10}$ alkane linking group (or divalent linear or branched $C_1$-$C_8$ alkane linking group, or divalent linear or branched $C_1$-$C_4$ alkane linking group).

With reference to $R^8$ of Formula (IV), the term "linear or branched fluorinated alkyl" means an alkyl group in which at least one, and less than all, available hydrogens have been replaced with a fluoro group (F).

Non-limiting examples of linear or branched divalent alkane groups from which $R^4$ of Formula (II), $R^6$ of Formula (III), and $R^7$ of Formula (IV) can each be independently selected include, divalent ethane, divalent linear or branched divalent propane, divalent linear or branched butane, divalent linear or branched pentane, and divalent linear or branched hexane.

In accordance with some embodiments of the present invention, and with reference to Formula (I) and Formula (II), $R^1$, $R^2$, $R^3$, and $R^5$ are in each case independently selected from the anion group represented by Formula (III) or the anion group represented by Formula (IV).

For purposes of non-limiting illustration, the cathodic component having cationic charge according to the present invention, such as represented by Formula (I) where $R^1$ and $R^2$ are each selected from a group represented by Formula (III), can be prepared by N-alkylation of one mole of 4,4'-bipyridine with two moles of a cyclic sulfonate ester, such as, but not limited to, 1,3-propane sultone and/or 1,4-butane sultone. A more detailed description of a related synthetic procedure is provided in the examples further herein.

For purposes of non-limiting illustration, the cathodic component having cationic charge according to the present invention, such as represented by Formula (I) where only $R^1$ is selected from a group represented by Formula (III), and $R^2$ is selected from linear or branched alkyl, optionally substituted cycloalkyl, or optionally substituted aryl, can be prepared by N-alkylation of one mole of an N-substituted 4,4'-bipyridinium mono-salt with one mole of a cyclic sulfonate ester, such as, but not limited to, 1,3-propane sultone and/or 1,4-butane sultone. The N-substituent of the N-substituted 4,4'-bipyridinium mono-salt is selected from linear or branched alkyl, optionally substituted cycloalkyl, or optionally substituted aryl.

For purposes of further non-limiting illustration, the cathodic component having cationic charge according to the present invention, such as represented by Formula (I) where $R^1$ and $R^2$ are each selected from a group represented by Formula (IV), can be prepared by reacting one mole of 4,4'-bipyridine with two moles of a ((chloroalkyl)sulfonyl) ((fluoroalkyl or perfluoroalkyl)sulfonyl)amide salt.

For purposes of additional non-limiting illustration, the cathodic component having cationic charge according to the present invention, such as represented by Formula (I) where only $R^1$ is selected from a group represented by Formula (IV), and $R^2$ is selected from linear or branched alkyl, optionally substituted cycloalkyl, or optionally substituted aryl, can be prepared by reacting one mole of an N-substituted 4,4'-bipyridinium mono-salt with one mole of a ((chloroalkyl)sulfonyl)((fluoroalkyl or perfluoroalkyl)sulfonyl) amide salt. The N-substituent of the N-substituted 4,4'-bipyridinium mono-salt is selected from linear or branched alkyl, optionally substituted cycloalkyl, or optionally substituted aryl.

In accordance with some embodiments of the present invention, the anodic component includes an anodic component anion selected from at least one anodic component anion represented by the following Formula (V) or Formula (VI), (V)

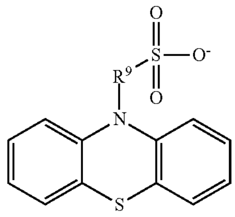

(VI)

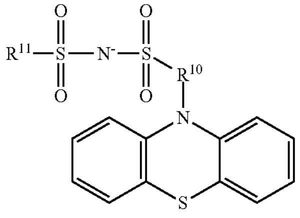

With reference to Formula (V), $R^9$ is selected from divalent linear or branched alkane linking group. With reference to Formula (VI), $R^{10}$ is selected from divalent linear or branched alkane linking group, and $R^{11}$ is selected from fluorine, linear or branched fluorinated alkyl, or linear or branched perfluorinated alkyl.

The anodic component anion can be described as including an anodic portion (group or moiety), such as a (10H-phenothiazin-10-yl) moiety, and an anion that is covalently bonded to the anodic moiety, such as a sulfonate anion or a triflimide anion. With some further embodiments, the anion of the anodic component anion is covalently bonded to the anodic group or moiety by a divalent linear or branched alkane linking group. With some further embodiments, the anodic component anion is an anodically-coloring electrochromic compound or group having an anion covalently bonded thereto.

With reference to $R^{11}$ of Formula (VI), the term "linear or branched fluorinated alkyl" means an alkyl group in which at least one, and less than all, available hydrogens have been replaced with a fluoro group (F).

With further reference to Formula (V), and in accordance with some embodiments, $R^9$ is selected from divalent linear or branched $C_1$-$C_{10}$ alkane linking group (or divalent linear or branched $C_1$-$C_8$ alkane linking group, or divalent linear or branched $C_1$-$C_5$ alkane linking group). With further reference to Formula (VI), and with some embodiments, $R^{10}$ is selected from divalent linear or branched $C_1$-$C_{10}$ alkane linking group (or divalent linear or branched $C_1$-$C_8$ alkane linking group, or divalent linear or branched $C_1$-$C_5$ alkane linking group), and $R^{11}$ is selected from fluorine, linear or branched fluorinated $C_1$-$C_{10}$ alkyl (or linear or branched fluorinated $C_1$-$C_8$ alkyl, or linear or branched fluorinated $C_1$-$C_5$ alkyl), or linear or branched perfluorinated $C_1$-$C_{10}$ alkyl (or linear or branched perfluorinated $C_1$-$C_8$ alkyl, or linear or branched perfluorinated $C_1$-$C_5$ alkyl).

With some non-limiting embodiments, $R^9$ of Formula (V) and $R^{10}$ of Formula (VI) are each independently selected from divalent methane, divalent ethane, divalent linear or branched propane, divalent linear or branched butane, and divalent linear or branched pentane. With some further non-limiting embodiments, $R^{11}$ of Formula (VI) is selected from fluorinated or perfluorinated versions or derivatives of methyl, ethyl, linear or branched propyl, linear or branched butyl, and linear or branched pentyl.

In accordance with some embodiments, the cathodic component having cationic charge and the anodic component anion, selected from at least one anodic component anion represented by the following Formula (V) or Formula (VI), together have a net neutral charge.

Reference herein to counter-ions (such as counter-cations and/or counter-anions) of a component, with some embodiments, means the counter-ions of the component when it is prepared separately from and/or prior to combining with the electrochromic layer and/or electrochromic composition of the present invention.

For purposes of non-limiting illustration, and in accordance with some embodiments: the cathodic component having cationic charge, such as represented by Formula (I), where only $R^1$ is selected from a group represented by Formula (III), and $R^2$ is selected from linear or branched alkyl, optionally substituted cycloalkyl, or optionally substituted aryl; and the anodic component anion together have a net neutral charge, can be represented by the following Formula (VII), Formula (VII)

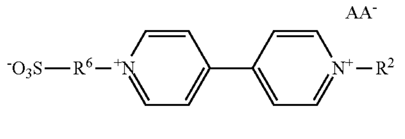

With reference to Formula (VII), $AA^-$ is an anodic component anion represented by Formula (V) or Formula (VI), as described previously herein. With further reference to Formula (VII), $R^6$ is as described previously herein with reference to Formula (III), and $R^2$ is selected from linear or branched alkyl, optionally substituted cycloalkyl, and optionally substituted aryl.

For purposes of non-limiting illustration, and in accordance with some embodiments: the cathodic component having cationic charge, such as represented by Formula (II), where $R^3$ and $R^5$ are each independently selected from a group represented by Formula (III); and the anodic component anion together have a net neutral charge, can be represented by the following Formula (VIII), Formula (VIII)

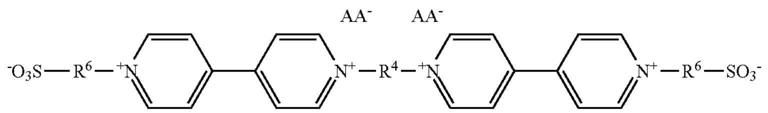

With reference to Formula (VIII), each $AA^-$ is independently an anodic component anion represented by Formula (V) or Formula (VI), as described previously herein. With further reference to Formula (VIII): each $R^6$ is independently as described previously herein with reference to Formula (III); and $R^4$ is a divalent linking group as described previously here with reference to Formula (II).

In accordance with some further embodiments, the anodic component, which includes the anodic component anion, further includes a counter-cation. Classes and examples of cations from which each counter-cation can be independently selected from include, but are not limited to: alkali metal cations, such as lithium cation ($Li^+$), sodium cation (Nat), and potassium cation ($K^+$); alkaline earth metal cations, such as $Mg^{2+}$, $Ca^{2+}$, and $Ba^{2+}$; optionally substituted nitrogen-containing aliphatic heterocycle ammonium cations, such as, optionally substituted N,N-disubstituted pyrrolidinium cations, optionally substituted N,N-disubstituted piperidinium cations, and optionally substituted N,N-disubstituted morpholinium cations; optionally substituted nitrogen-containing aromatic heterocycle ammonium cations such as, optionally substituted N-substituted pyridinium cations, optionally substituted N-substituted quinolinium cations, and optionally substituted N-substituted isoquinolinium cations; and tetrasubstituted ammonium cations, described in further detail below. The optional substituents of the classes and examples of ammonium cations can be selected from those classes and examples of substituents recited previously herein, such as, but not limited to, linear or branched alkyl groups, cycloalkyl groups, and aryl groups. The N-substituted and N,N-disubstituted groups of the ammonium cations can be selected from those classes and examples of substituents recited previously herein, such as, but not limited to, linear or branched alkyl groups, cycloalkyl groups, and aryl groups.

With some embodiments, the counter-cation of the anodic component is a mono-cation. In accordance with some further embodiments, the counter-cation of the anodic component is selected from tetrasubstituted ammonium cations represented by the following Formula (C), Formula (C)

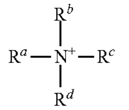

With reference to Formula (C), $R^a$, $R^b$, $R^c$, and $R^d$ are each independently selected from linear or branched alkyl, unsubstituted cycloalkyl, substituted cycloalkyl, unsubstituted aryl, and substituted aryl. With further reference to Formula (B), $R^a$, $R^b$, $R^c$, and $R^d$ are each independently selected from linear or branched $C_1$-$C_{10}$ alkyl, unsubstituted $C_3$-$C_7$ cycloalkyl, substituted $C_3$-$C_7$ cycloalkyl, unsubstituted phenyl, and substituted phenyl. The substituents of the substituted cycloalkyl and substituted phenyl groups can in each case be independently selected from those substituents as recited previously herein, such as, but not limited to linear or branched alkyl groups, cycloalkyl groups, and aryl groups.

With some embodiments, and with reference to Formula (B), each of $R^a$, $R^b$, $R^c$, and $R^d$ is independently selected from linear or branched alkyl. With some further embodiments, each of $R^a$, $R^b$, $R^c$, and $R^d$ of Formula (B) is independently selected from linear or branched $C_1$-$C_{10}$ alkyl (or linear or branched $C_1$-$C_8$ alkyl, or linear or branched $C_1$-$C_5$ alkyl).

Each counter-cation, of the anodic component, is independently selected from tetra(linear or branched alkyl)ammonium cation, with some embodiments. Each counter-cation, of the anodic component, is independently selected from tetra(linear or branched $C_1$-$C_{10}$ alkyl)ammonium cation, with some further embodiments.

The anodic component, with some embodiments, is composed of, or otherwise consists of: an anodic component anion selected from at least one anodic component anion represented by Formula (V) or Formula (VI); and a counter-cation, where the anodic component has an equal number of anions and counter-cations, and correspondingly a neutral charge.

In accordance with some embodiments, in addition to, or alternatively to, an anodic component anion having an anion covalently bonded thereto, such as represented by Formula (V) and/or Formula (VI), the anodic component of the electrochromic layer includes one or more further anodic electrochromic compounds, such as, but not limited to: ferrocene and/or ferrocene derivatives (in which at least one cyclopentadienyl ring thereof is substituted with at least one substituent, including those substituents recited previously herein); 5,10-dihydro-5,10-di(linear or branched $C_1$-$C_{10}$ alkyl)phenazine, such as 5,10-dihydro-5,10-dimethylphenazine; N-substitutedphenoxazine, such as N-phenylphenoxazine; and combinations thereof. In accordance with some embodiments, when a further anodic component in present (in addition to the anodic component anion having an anion covalently bonded thereto) a further cathodic component (or further appropriate amount of cathodic component) can also be present. The further cathodic component, with some embodiments, comprises one or more cathodic components, such as represented by Formulas (I) and/or (II), but in which $R^1$, $R^2$, $R^3$, and $R^5$ are in each case not selected from Formulas (III) and (IV).

In accordance with some embodiments of the present invention, the cathodic component further includes counter-anions. With some further embodiments, the cathodic component includes an equal number of cations and counter-anions (or anions), and correspondingly the cathodic component has a net neutral charge. Each counter-anion of the cathodic component, with some embodiments, is independently selected from the group consisting of $BF_4^-$, $PF_6^-$, $ClO_4^-$, $CF_3SO_3^-$, $(CF_3SO_2)_2N^-$, $(CF_3SO_2)_3C^-$, or $B(phenyl)_4^-$. With some embodiments, the counter-anions of the cathodic component do not include and are not selected from anodic component anions, such as represented by Formulas (V) and (VI).

In accordance with some embodiments of the present invention, the cathodic component having cationic charge is present in the electrochromic layer in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic layer.

The anodic component, such as but not limited to the anodic component having an anion covalently bonded thereto, with some embodiments, is present in the electrochromic layer in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic layer.

With some embodiments of the present invention, the electrochromic layer of the electrochromic device of the present invention, includes an electrolyte. The electrolyte includes, with some embodiments, at least one electrolyte anion and at least one electrolyte cation. The electrolyte of the electrochromic layer includes, with some embodiments, an equal number of electrolyte anions and electrolyte cations, and correspondingly has a net neutral charge.

With some embodiments, the electrolyte of the electrochromic layer includes at least one electrolyte anion, where each electrolyte anion is independently selected from chloride, hexafluorophosphate, and bis(perfluoro(linear or branched $C_1$-$C_6$ alkysulfonyl)imide. With some further embodiments, the electrolyte of the electrochromic layer includes at least one electrolyte cation, where each electrolyte cation is independently selected from: sodium; potassium; lithium; ammonium cations, such as, tetra(linear or branched $C_1$-$C_6$)ammonium, and tri($C_5$-$C_8$ cycloalkyl)-(linear or branched $C_1$-$C_6$ alkyl)ammonium; 1-(linear or branched $C_1$-$C_6$ alkyl)-3-(linear or branched $C_1$-$C_6$ alkyl) imidazolium; 1-(linear or branched $C_1$-$C_6$ alkyl)-1-(linear or branched $C_1$-$C_6$ alkyl)pyrrolidinium; 1-(linear or branched $C_1$-$C_6$ alkyl)-1-(linear or branched $C_1$-$C_6$ alkyl)piperidinium; or phosphonium cations, such as, but not limited to tetra(linear or branched $C_1$-$C_6$ alkyl)phosphonium, or tri($C_5$-$C_8$ cycloalkyl)-(linear or branched $C_1$-$C_6$ alkyl)phosphonium.

The electrolyte of the electrochromic layer, with some embodiments includes: at least one electrolyte anion, where each electrolyte anion is independently selected from bis (perfluoro(linear or branched $C_1$-$C_6$ alkysulfonyl)imide; and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, or 1-(linear or branched $C_1$-$C_6$ alkyl)-1-(linear or branched $C_1$-$C_6$ alkyl) piperidinium.

The electrolyte of the electrochromic layer, with some further embodiments includes: at least one electrolyte anion, where each electrolyte anion is bis(trifluromethylsulfonyl) imide; and at least one electrolyte cation, where each electrolyte cation is independently selected from 1-ethyl-3-methylimidazolium, 1-butyl-3-methylimidazolium, 1-methyl-1-butylpyrrolidinium, and 1-methyl-1-propylpiperidinium.

The electrolyte, with some embodiments, is present in the electrochromic layer in an amount of from 1 percent by weight to 75 percent by weight, or from 5 percent by weight to 50 percent by weight, or from 10 percent by weight to 30 percent by weight, the percent weights in each case being based on the total weight of the electrochromic layer.

In accordance with some further embodiments, the electrochromic layer of the present invention includes a solvent. With some additional embodiments, the solvent is present, in the electrochromic layer, alternatively to or in addition to the electrolyte. The solvent can, with some embodiments, include at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides. While not intending to be bound by any theory, and in accordance with some embodiments, it is believed that the solvent acts, at least in part, as a plasticizer within (or plasticizes) the electrochromic layer. The solvent, with some embodiments, is present in the electrochromic layer in an amount of from 10 to 75 percent by weight, or from 20 to 60 percent by weight, the percent weights in each case being based on the total weight of the electrochromic layer and the solvent.

The electrochromic layer, of the electrochromic devices of the present invention, includes a polymer matrix. The polymer matrix includes at least one polymer. The polymer matrix, with some embodiments, is a gelled polymer matrix, a crosslinked polymer matrix, and/or a thermoplastic polymer matrix.

With some embodiments, the polymer matrix includes a polymer, where the polymer includes at least one of poly ((meth)acrylonitrile), poly(vinylidene fluoride), poly(vinylidene fluoride-co-perfluoro(linear or branched $C_1$-$C_6$ alkylene)), poly((linear or branched $C_1$-$C_8$ alkyl)(meth)acrylate), or poly(diallyldimethylammonium $X^-$), wherein each $X^-$ independently is an anion represented by the following Formula (A),

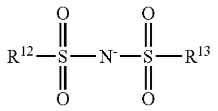

(A)

With reference to Formula (A), $R^{12}$ and $R^{13}$ are each independently selected from fluorine, linear or branched fluorinated alkyl, or linear or branched perfluorinated alkyl.

With reference to Formula (A), the term "linear or branched fluorinated alkyl" means an alkyl group in which at least one, and less than all, available hydrogens have been replaced with a fluoro group (F).

With some embodiments, $R^{12}$ and $R^{13}$ of Formula (A) are each independently selected from fluorine, linear or branched $C_1$-$C_{10}$ fluorinated alkyl, or linear or branched $C_1$-$C_{10}$ perfluorinated alkyl.

With some further embodiments, $R^{12}$ and $R^{13}$ of Formula (A) are each independently selected from linear or branched $C_1$-$C_5$ perfluorinated alkyl.

With some additional embodiments, $R^{12}$ and $R^{13}$ of Formula (A) are each trifluoromethyl, and the polymer of the polymer matrix includes poly((diallyldimethylammonium) bis(trifluoromethanesulfonyl)imide)), also referred to herein as poly((diallyldimethylammonium) bis(trifluoromethane) sulfonimide.

The poly(diallyldimethylammonium $X^-$) polymer of the polymer matrix, of the electrochromic layer, can also be referred to herein as a poly((diallyldimethylammonium bis (substituted-sulfonyl)imide anion)), where the substituent of each substituted-sulfonyl portion thereof is independently selected from $R^{12}$ and $R^{13}$ as described with reference to Formula (A).

With some embodiments, the poly(diallyldimethylammonium $X^-$) polymer of the polymer matrix, can be described with reference to the following Formula (D), (D)

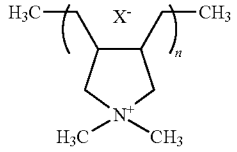

With reference to Formula (D), each $X^-$ independently is an anion represented by Formula (A), as described previously herein. In light of difficulties in determining the Mn of poly(diallyldimethylammonium) polymers, such as represented by Formula (D), and without intending to be bound by any theory, it is estimated that n of Formula (D) is, with some embodiments, at least 2, such as from 2 to at least 1000, or from 50 to at least 1000.

The poly(diallyldimethylammonium $X^-$) polymer, with some embodiments of the present invention, has a Mw of: less than 100 kDa; or from 200 to 350 kDa; or from 400 to 500 kDa.

The poly(diallyldimethylammonium $X^-$) polymer, with some embodiments, can be prepared in accordance the non-limiting synthetic description provided in the examples further herein.

In accordance with some embodiments of the present invention, the polymer matrix of the electrochromic layer includes a polymer, where the polymer comprises poly (diallyldimethylammonium $X^-$), where each $X^-$ independently is an anion represented by Formula (A), as described above.

The polymer matrix, with some embodiments, is present in the electrochromic layer in an amount of from 5 percent by weight to 80 percent by weight, or from 10 percent by weight to 60 percent by weight, or from 15 percent by weight to 50 percent by weight, the percent weights in each case being based on the total weight of the electrochromic layer.

The electrochromic layer of the electrochromic devices of the present invention can, with some embodiments, further include one or more art-recognized optional additives, such as, but not limited to, thermal stabilizers, UV stabilizers, rheology modifiers, static coloring agents (such as static tints and/or static dyes), kinetic additives (that accelerate electrode reaction) and combinations thereof. A non-limiting class of art-recognized thermal stabilizers are phenols, such as 2,6-ditertiarybutylphenol and compounds including 2,6-ditertiarybutylphenol groups or moieties. A non-limiting class of art-recognized UV stabilizers are hindered amine light stabilizers (HALS), such as 2,2,6,6-tetramethylpiperidine and compounds including 2,2,6,6-tetramehtylpiperidine groups or moieties. Static coloring agents include coloring agents for which the absorption spectrum thereof does not change in response to actinic radiation (such as UV and/or visible light) or the application of an electric potential, and do not include photochromic compounds and electrochromic compounds. A non-limiting class of kinetic additives includes salts, such as: alkali and alkaline earth metal salts of perchlorates, tetrafluoroborates, and hexafluorophosphates; and tetraalkylammonium salts. Non-limiting examples of rheology modifies include: dialkoxyacetophenones, such as 3',4'dimethoxyacetophenone; and optionally substituted cycloalkylarylketones, such as 1-hydroxycyclohexyl phenyl ketone. Each optional additive can be present in any suitable active amount, such as from 0.05 percent by weight to 5 percent by weight, based on the total solids weight of the electrochromic layer (including the weight of the optional additive(s)).

The electrochromic layer of the electrochromic devices of the present invention can have any suitable thickness. With some embodiments, the electrochromic layer has a thickness of from 50 micrometers to 800 micrometers.

For purposes of non-limiting illustration, an electrochromic device (3) according to the present invention is depicted in FIG. 1. Electrochromic device (3) includes a first substrate (11) having a first surface (14) and a second surface (17). First surface (14) of first substrate (11) includes a first transparent electrode layer (20), which is electrically conductive. First transparent electrode layer (20) resides over at least a portion of first surface (14) of first substrate (11). With some embodiments, first transparent electrode layer (20) is in the form of one or more patterns (such as, one or more designs and/or indicia) over first surface (14) of first substrate (11). With some further embodiments, first transparent electrode layer (20) forms a substantially continuous layer over first surface (14) of first substrate (11). First transparent electrode layer (20) is, with some embodiments, in electrical contact with at least one first electrical conductor (21), which can be a first electrically conductive wire.

Electrochromic device (3) includes a second substrate (23) having a first surface (26) and a second surface (29). First surface (26) of second substrate (23) includes a second transparent electrode layer (32), which is electrically conductive. Second transparent electrode layer (32) resides over at least a portion of first surface (26) of second substrate (23). With some embodiments, second transparent electrode layer (32) is in the form of one or more patterns (such as, one or more designs and/or indicia) over first surface (26) of second substrate (23). With some further embodiments, second transparent electrode layer (32) forms a substantially continuous layer over first surface (26) of second substrate (23). Second transparent electrode layer (32) is, with some embodiments, in electrical contact with at least one second electrical conductor (33), which can be a second electrically conductive second wire.

With further reference to electrochromic device (3) of FIG. 1, first transparent electrode layer (20) and second transparent electrode layer (32) are in opposing spaced facing opposition relative to each other.

Electrochromic device (3) further includes an electrochromic layer (35) that is interposed between first transparent electrode layer (20) and second transparent electrode layer (32). With some embodiments, electrochromic layer (35) is interposed between and in abutting relationship with first transparent electrode layer (20) and second transparent electrode layer (32).

The first substrate and the second substrate of the electrochromic devices are, with some embodiments of the present invention, each independently selected from transparent substrates. Transparent substrates, from which the first and second substrates can each be independently selected, are with some embodiments, fabricated from materials including, but not limited to, silica glass, organic polymers (such as, but not limited to, polycarbonate polymers), and combinations thereof. With some embodiments, the transparent substrates, from which the first and second substrates can each be independently selected, are fabricated from materials including silica glass. The first and second substrates can each independently have any suitable thickness. With some embodiments, the first and second substrates each independently have a thickness of from 1 mm to 25 mm, or from 2 mm to 10 mm.

The first and second transparent electrode layers of the electrochromic devices of the present invention, with some embodiments, include electrically conductive inorganic oxides, electrically conductive organic materials, electrically conductive metals, and/or electrically conductive carbon, such as carbon nanotubes and/or graphene. Examples of electrically conductive inorganic oxides, include, but are not limited to: tin oxide, which can be doped with a doping material, such as indium; and zinc oxide, which can further include, for example, aluminum. Examples of electrically conductive organic materials include, but are not limited to, poly(3,4-ethylenedioxythiophene), poly(4,4-dioctyl cyclopentadithiophene), and poly(3,4-ethylenedioxythiophene): poly(styrene sulfonate). The first and second transparent electrode layers, with some embodiments, can each independently be in the form of a grid of metal wires, a grid of carbon nanotubes, and/or a layer of graphene. With some embodiments, the first and second transparent electrode layers are each independently selected from semi-transparent metal layers. With some further embodiments, one of the first and second transparent electrode layers includes (or has associated therewith) a reflective metal layer (including, for example, aluminum, gold, and/or silver) and the electrochromic device is a reflective electrochromic device, such as a controllably reflective mirror.

In accordance with some embodiments, the first and second electrode layers of the electrochromic devices of the present invention, each independently include an electrically conductive material selected from indium-tin-oxide, poly(3, 4-ethylenedioxythiophene):poly(styrene sulfonate), or combinations thereof.

The first and second electrode layers of the electrochromic devices, in accordance with some embodiments of the present invention, can each independently have any suitable thickness, provided they are both transparent and electrically conductive. With some embodiments, the first and second electrode layers of the electrochromic devices of the present invention, each independently have a thickness of from 0.01 micrometers to 10 micrometers.

Examples of articles, such as articles of manufacture, that may include or be defined by the electrochromic devices of the present invention include, but are not limited to: energy efficient and/or privacy transparencies (or windows), such as architectural and transportation transparencies or windows; mirrors, such as rearview mirrors; optical filters; and ophthalmic articles, such as corrective lenses, non-corrective lenses, magnifying lenses, protective lenses, and visors; and any other article or application where variable and controllable light transmission and/or color is desired.

The present invention also relates to an electrochromic composition that includes: (i) a cathodic component; (ii) an anodic component; (iii) an optional electrolyte; (iv) a polymeric thickener; and (v) a solvent. The cathodic component of the electrochromic compositions includes at least one of a 1,1'-disubstituted-4,4'-dipyridinium cation represented by Formula (I) as described previously herein, or a 1,1-(alkane-alpha, omega-diyl)-bis-(1'-substituted-4,4'-dipyridinium) cation represented by Formula (II) as described previously herein. As described previously herein, there is provided that for Formula (I), at least one of $R^1$ and $R^2$ is independently selected from the group represented by Formula (III) or the group represented by Formula (IV). As additionally described previously herein, there is provided that for Formula (II), at least one of $R^3$ and $R^5$ is independently selected from the group represented by Formula (III) or the group represented by Formula (IV).

The cathodic component, anodic component, anodic component anion, optional electrolyte, and polymer thickener of the electrochromic composition are each as describe previously herein with regard to the electrochromic device of the present invention.

The electrochromic composition of the present invention includes a solvent. With some embodiments, the solvent of the electrochromic composition includes at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides.

In accordance with some embodiments, the anodic component, which includes the anodic component anion, further includes a counter-cation. Classes and examples of cations from which each counter-cation can be independently selected from those classes and examples a recited previously herein with regard to the electrochromic device. With some embodiments of the electrochromic composition of the present invention, each counter-cation is independently selected from tetra(linear or branched alkyl)ammonium cation. In accordance with some further embodiments, each counter-cation is independently selected from tetra(linear or branched $C_1$-$C_{10}$ alkyl)ammonium cation.

With some embodiments, the cathodic component of the electrochromic composition further includes counter-anions, wherein each counter-anion of the cathodic component is selected from the group consisting of $BF_6^-$, $PF_6^-$, $ClO_4^-$, $CF_3SO_3^-$, $(CF_3SO_2)_2N^-$, $(CF_3SO_2)_3C^-$, or $B(phenyl)_4^-$. With some embodiments, the counter-anions of the cathodic component of the electrochromic composition do not include and are not selected from anodic component anions, such as represented by Formulas (V) and (VI).

The cathodic component having cationic charge, with some embodiments, is present in the electrochromic composition in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic composition.

The anodic component, such as but not limited to the anodic component having an anion covalently bonded thereto, is present in the electrochromic composition, with some embodiments, in an amount of from 0.25 percent by weight to 6.25 percent by weight, or from 0.5 percent by weight to 5 percent by weight, or from 1 percent by weight to 3 percent by we, the percent weights in each case being based on the total weight of the electrochromic composition.

The electrolyte is present in the electrochromic composition, with some embodiments, in an amount of from 1 percent by weight to 75 percent by weight, or from 5 percent by weight to 50 percent by weight, or from 10 percent by weight to 30 percent by weight, the percent weights in each case being based on the total weight of the electrochromic composition.

The polymeric thickener is present in the electrochromic composition, with some embodiments, in an amount of 5 percent by weight to 80 percent by weight, or from 10 percent by weight to 60 percent by weight, or from 15 percent by weight to 50 percent by weight, the percent weights in each case being based on the total weight of the electrochromic composition.

The solvent is present in the electrochromic composition, with some embodiments, in and amount of from 10 to 75 percent by weight, or from 20 to 60 percent by weight, or from 25 percent by weight to 50 percent by weight, the percent weights in each case being based on the total weight of the electrochromic composition.

The electrochromic composition of the present invention can, with some embodiments, include one or more art-recognized optional additives, such as, but not limited to, thermal stabilizers, UV stabilizers, rheology modifiers, static coloring agents (such as static tints and/or static dyes), kinetic additives (that accelerate electrode reaction) and combinations thereof. The optional additives are in each case as described previously herein with regard to the electrochromic device of the present invention. Each optional additive can be present in the electrochromic composition in any suitable active amount, such as from 0.05 percent by weight to 5 percent by weight, based on the total weight of the electrochromic composition (including the weight of the optional additive(s)).

In accordance with some embodiments of the present invention, the electrochromic layer of the electrochromic device is formed from the electrochromic composition of the present invention. In accordance with some embodiments of the present invention, formation of the electrochromic composition and electrochromic layer includes the following steps. First, all components of the electrochromic composition, other than the polymeric thickener, are mixed under sheer (such as with an impeller) until a homogenous mixture is formed. Secondly, the polymeric thickener is added, and the combination is subjected to homogenization, which results in the formation of a thick slurry. A liquid film of the thick slurry is formed, such as using a doctor blade or draw-down bar, on a sacrificial or temporary liner (composed of polyethylene terephthalate, in some embodiments). The liquid film while on the sacrificial/temporary liner is subjected to elevated temperature, such as from 60° to 90° C. for 3 to 10 minutes, which results in the formation of a solidified film/layer, which is the electrochromic layer. The solidified film/electrochromic layer, is separated from the sacrificial/temporary liner (which is discarded), cut to size (if necessary), and placed over or onto a first transparent electrode layer of a first substrate. The second transparent electrode of a second substrate is positioned over or onto the other (or facing/exposed) side of the electrochromic layer, to form a stack that includes the first substrate, the first transparent electrode, the electrochromic layer, the second transparent electrode, and the second substrate. The stack may further include electrical connectors that are in separate electrical contact with the first and second transparent electrodes. The stack (with an optional gasket surrounding the outer edges of at least the electrochromic layer) is subjected to vacuum lamination, with the concurrent application of elevated temperature, such as from 110° C. to 200° C., for a period of time, such as from 10 to 30 minutes. After cooling, the so formed electrochromic device is removed from vacuum lamination device.

In accordance with some further embodiments, when the polymeric thickener of the electrochromic composition includes, or is, poly(diallyldimethylammonium $X^-$), as described previously herein, the electrochromic layer can be prepared therefrom in accordance with the following general description. First, all components of the electrochromic composition, other than the polymeric thickener, are mixed under sheer (such as with an impeller) until a homogenous mixture is formed. Secondly, the polymeric thickener is added and mixed to form a viscous paste. The viscous paste is compounded and extruded at elevated temperature into the desired form, such as a film (in some embodiments this can be accomplished through a heated extrusion screw and slot die). This film can be deposited onto a sacrificial or temporary liner (e.g., composed of polyethylene terephthalate, in some embodiments) or extruded directly onto a first transparent electrode layer of a first substrate. For embodiments that use a sacrificial liner, the film/electrochromic layer, is then separated from the sacrificial/temporary liner (which is discarded), cut to size (if necessary), and placed over or onto a first transparent electrode layer of a first substrate. The second transparent electrode of a second substrate is positioned over or onto the other (or facing/exposed) side of the electrochromic layer, to form a stack that includes the first substrate, the first transparent electrode, the electrochromic layer, the second transparent electrode, and the second substrate. The stack can optionally further include electrical connectors that are in separate electrical contact with the first and second transparent electrodes. The stack (with an optional gasket surrounding the outer edges of at least the electrochromic layer) is subjected to vacuum lamination, with the concurrent application of elevated temperature, such as from 110° C. to 200° C., for a period of time, such as from 10 to 30 minutes. After cooling, the so formed electrochromic device is removed from vacuum lamination device.

The present invention can further be characterized by one or more of the following non-limiting clauses.

Clause 1: An electrochromic device comprising:

(a) a first substrate having a surface comprising a first transparent electrode layer;

(b) a second substrate having a surface comprising a second transparent conductive electrode layer, wherein said first transparent electrode layer and said second transparent electrode layer are in opposing spaced opposition; and (c) an electrochromic layer interposed between said first transparent electrically conductive electrode layer and said second transparent electrically conductive electrode layer, wherein said electrochromic layer comprises, (i) a cathodic component, (ii) an anodic component, (iii) an optional electrolyte, and (iv) a polymer matrix, wherein said cathodic component comprises a cathodic component having cationic charge selected from at least one of a 1,1'-disubstituted-4,4'-dipyridinium cation represented by the following Formula (I), or a 1,1-(alkane-alpha, omega-diyl)-bis-(1'-substituted-4,4'-dipyridinium) cation represented by the following Formula (II), (I)

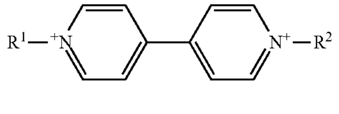

(II)

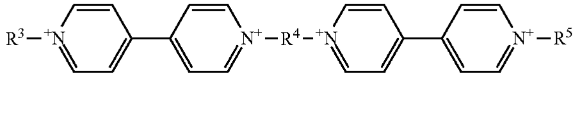

wherein for Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by the following Formula (III), $R^6—SO_3^-$ (III), and a group represented by the following Formula (IV), (IV)

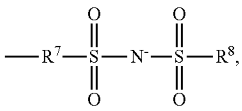

wherein for Formula (III) and Formula (IV), $R^6$ and $R^7$ are in each case independently selected from divalent linear or branched alkane linking group, and for Formula (IV), $R^8$ is selected from fluorine, linear or branched fluorinated alkyl, or linear or branched perfluorinated alkyl, and for Formula (II), $R^4$ is selected from divalent linear or branched alkane linking group, provided that for Formula (I), at least one of $R^1$ and $R^2$ is independently selected from said group represented by Formula (III) or said group represented by Formula (IV), and provided that for Formula (II), at least one of $R^3$ and $R^5$ is independently selected from said group represented by Formula (III) or said group represented by Formula (IV).

Clause 2: The electrochromic device of clause 1, wherein for Formula (I) and Formula (II), $R^1$, $R^2$, $R^3$, and $R^5$ are in each case independently selected from linear or branched $C_1$-$C_{10}$ alkyl, unsubstituted $C_3$-$C_7$ cycloalkyl, substituted $C_3$-$C_7$ cycloalkyl, unsubstituted phenyl, substituted phenyl, said group represented by Formula (III), and said group represented by Formula (IV), wherein for Formula (III) and Formula (IV), $R^6$ and $R^7$ are in each case independently selected from divalent linear or branched $C_1$-$C_{10}$ alkane linking group, and for Formula (IV), $R^8$ is selected from fluorine, linear or branched fluorinated $C_1$-$C_{10}$ alkyl, or linear or branched perfluorinated $C_1$-$C_{10}$ alkyl, and for Formula (II), $R^4$ is selected from divalent linear or branched $C_1$-$C_{10}$ alkane linking group.

Clause 3: The electrochromic device of clause 1 or clause 2, wherein said anodic component comprises an anodic component anion selected from at least one anodic component anion represented by the following Formula (V) or Formula (VI), (V)

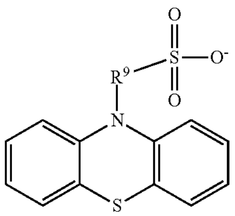

-continued (VI)

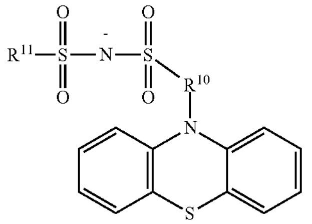

wherein for Formula (V), $R^9$ is selected from divalent linear or branched alkane linking group, and for Formula (VI), $R^{10}$ is selected from divalent linear or branched alkane linking group, and $R^{11}$ is selected from fluorine, linear or branched fluorinated alkyl, or linear or branched perfluorinated alkyl.

Clause 4: The electrochromic device of clause 3, wherein for Formula (V), $R^9$ is selected from divalent linear or branched $C_1$-$C_{10}$ alkane linking group, and for Formula (VI), $R^{10}$ is selected from divalent linear or branched $C_1$-$C_{10}$ alkane linking group, and $R^{11}$ is selected from fluorine, linear or branched fluorinated $C_1$-$C_{10}$ alkyl, or linear or branched perfluorinated $C_1$-$C_{10}$ alkyl.

Clause 5: The electrochromic device of clause 3 or clause 4, wherein said cathodic component having cationic charge and said anodic component anion, selected from at least one anodic component anion represented by Formula (V) or Formula (VI), together have a net neutral charge.

Clause 6: The electrochromic device of clause 3 or clause 4, wherein said anodic component further comprises a counter-cation.

Clause 7: The electrochromic device of clause 6, wherein each counter-cation is independently selected from optionally substituted nitrogen-containing aliphatic heterocycle ammonium cations, optionally substituted nitrogen-containing aromatic heterocycle ammonium cations, tetrasubstituted ammonium cations, or combinations thereof.

Clause 8: The electrochromic device of clause 6 or clause 7, wherein each counter-cation is independently selected from tetrasubstituted ammonium cations represented by the following Formula (C), Formula (C)

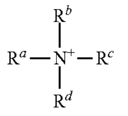

wherein $R^a$, $R^b$, $R^c$, and $R^d$ are each independently selected from linear or branched alkyl, unsubstituted cycloalkyl, substituted cycloalkyl, unsubstituted aryl, and substituted aryl.

Clause 9: The electrochromic device of clause 8, wherein $R^a$, $R^b$, $R^c$, and $R^d$ are each independently selected from linear or branched $C_1$-$C_{10}$ alkyl, unsubstituted $C_3$-$C_7$ cycloalkyl, substituted $C_3$-$C_7$ cycloalkyl, unsubstituted phenyl, or substituted phenyl.

Clause 10: The electrochromic device of clause 8 or clause 9, wherein $R^a$, $R^b$, $R^c$, and $R^d$ are each independently selected from linear or branched $C_1$-$C_{10}$ alkyl.

Clause 11: The electrochromic device of any one of clauses 6, 7, 8, 9, or 10, wherein each counter-cation is independently selected from tetra(linear or branched alkyl) ammonium cation.

Clause 12: The electrochromic device of any one of clauses 6, 7, 8, 9, 10, or 11, wherein each counter-cation is independently selected from tetra(linear or branched $C_1$-$C_{10}$ alkyl)ammonium cation.

Clause 13: The electrochromic device of any one of clauses 1, 2, 3, 4, 6, 7, 8, 9, 10, 11, or 12, wherein said cathodic component further comprises counter-anions, wherein each counter-anion of the cathodic component is selected from the group consisting of $BF_4^-$, $PF_6^-$, $ClO_4^-$, $CF_3SO_3^-$, $(CF_3SO_2)_2N^-$, $(CF_3SO_2)_3C^-$, or $B(phenyl)_4^-$.

Clause 14: The electrochromic device of any one of clauses 1, 2, 3, 4, 5, 6, 7, 8, 9, 10, 11, 12, or 13, wherein said electrolyte is present and comprises, at least one electrolyte anion, wherein each electrolyte anion is independently selected from bis(perfluoro(linear or branched $C_1$-$C_6$ alkylsulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)piperidinium, phosphonium cations, such as, but not limited to tetra(linear or branched $C_1$-$C_6$ alkyl)phosphonium, or tri($C_5$-$C_8$ cycloalkyl)-(linear or branched $C_1$-$C_6$ alkyl)phosphonium, or ammonium cations, such as, but not limited to, tetra(linear or branched $C_1$-$C_6$)ammonium, and tri($C_5$-$C_8$ cycloalkyl)-(linear or branched $C_1$-$C_6$ alkyl)ammonium.

Clause 15: The electrochromic device of any one of clauses 1, 2, 3, 4, 5, 6, 7, 8, 9, 10, 11, 12, 13, or 14, wherein said polymer matrix comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), poly((linear or branched C alkyl)(meth)acrylate), or poly(diallyldimethylammonium $X^-$), wherein each $X^-$ independently is an anion represented by the following Formula (A), (A)

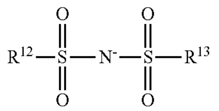

wherein $R^{12}$ and $R^{13}$ are each independently selected from fluorine, linear or branched fluorinated alkyl (or linear or branched fluorinated $C_1$-$C_{10}$ alkyl; or linear or branched fluorinated $C_1$-$C_8$ alkyl; or linear or branched fluorinated $C_1$-05 alkyl), or linear or branched perfluorinated alkyl (or linear or branched perfluorinated $C_1$-$C_{10}$ alkyl; or linear or branched perfluorinated $C_1$-$C_8$ alkyl; or linear or branched perfluorinated $C_1$-05 alkyl).

Clause 16: The electrochromic device of any one of clauses 1, 2, 3, 4, 5, 6, 7, 8, 9, 10, 11, 12, 13, 14, or 15, wherein said polymer matrix comprises a polymer, wherein said polymer comprises poly(diallyldimethylammonium $X^-$), wherein each $X^-$ independently is an anion represented by the following Formula (A), (A)

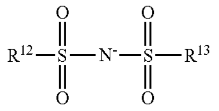

wherein $R^{12}$ and $R^{13}$ are each independently selected from fluorine, linear or branched fluorinated alkyl (or linear or branched fluorinated $C_1$-$C_{10}$ alkyl; or linear or branched fluorinated $C_1$-$C_8$ alkyl; or linear or branched fluorinated $C_1$-$C_5$ alkyl), or linear or branched perfluorinated alkyl (or linear or branched perfluorinated $C_1$-$C_{10}$ alkyl; or linear or branched perfluorinated $C_1$-$C_8$ alkyl; or linear or branched perfluorinated $C_1$-$C_5$ alkyl).

Clause 17: An article of manufacture comprising said electrochromic device of any one of clauses 1, 2, 3, 4, 5, 6, 7, 8, 9, 10, 11, 12, 13, 14, 15, or 16, wherein said article of manufacture is selected from, energy efficient transparencies, privacy transparencies, mirrors, optical filters, or ophthalmic articles.

Clause 18: An electrochromic composition comprising, (i) a cathodic component, (ii) an anodic component, (iii) an optional electrolyte, (iv) a polymeric thickener, and (v) a solvent, wherein said cathodic component comprises a cathodic component having cationic charge selected from at least one of a 1,1'-disubstituted-4,4'-dipyridinium cation represented by the following Formula (I), or a 1,1-(alkane-alpha, omega-diyl)-bis-(1'-substituted-4,4'-dipyridinium) cation represented by the following Formula (II), (I)

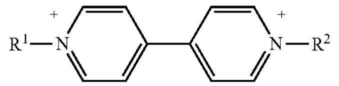

(II)

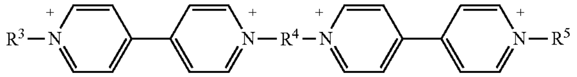

wherein for Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by the following Formula (III), $R^6$—$SO_3^-$ (III), and a group represented by the following Formula (IV), (IV)

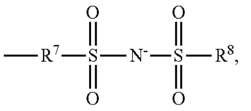

wherein for Formula (III) and Formula (IV), $R^6$ and $R^7$ are in each case independently selected from divalent linear or branched alkane linking group, and for Formula (IV), $R^8$ is selected from fluorine, linear or branched fluorinated alkyl, or linear or branched perfluorinated alkyl, and for Formula (II), $R^4$ is selected from divalent linear or branched alkane linking group, provided that for Formula (I), at least one of $R^1$ and $R^2$ is independently selected from said group represented by Formula (III) or said group represented by Formula (IV), and provided that for Formula (II), at least one of $R^3$ and $R^5$ is independently selected from said group represented by Formula (III) or said group represented by Formula (IV).

Clause 19: The electrochromic composition of clause 18, wherein for Formula (I) and Formula (II), $R^1$, $R^2$, $R^3$, and $R^5$ are in each case independently selected from linear or branched $C_1$-$C_{10}$ alkyl, unsubstituted $C_3$-$C_7$ cycloalkyl, substituted $C_3$-$C_7$ cycloalkyl, unsubstituted phenyl, and substituted phenyl, said group represented by Formula (III), and said group represented by Formula (IV), wherein for Formula (III) and Formula (IV), $R^6$ and $R^7$ are in each case independently selected from divalent linear or branched $C_1$-$C_{10}$ alkane linking group, and for Formula (IV), $R^8$ is selected from fluorine, linear or branched fluorinated $C_1$-$C_{10}$ alkyl, or linear or branched perfluorinated $C_1$-$C_{10}$ alkyl, and for Formula (II), $R^4$ is selected from divalent linear or branched $C_1$-$C_{10}$ alkane linking group.

Clause 20: The electrochromic composition of Clause 18 or clause 19, wherein said anodic component comprises an anodic component anion selected from at least one anodic component anion represented by the following Formula (V) or Formula (VI), (V)

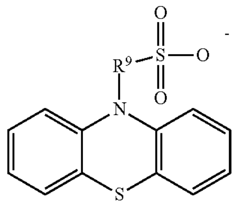

(VI)

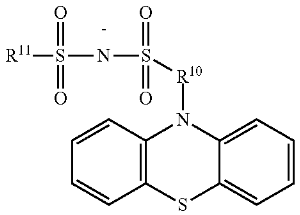

wherein for Formula (V), $R^9$ is selected from divalent linear or branched alkane linking group, and for Formula (VI), $R^{10}$ is selected from divalent linear or branched alkane linking group, and $R^{11}$ is selected from fluorine, linear or branched fluorinated alkyl, or linear or branched perfluorinated alkyl.

Clause 21: The electrochromic composition of clause 20, wherein for Formula (V), $R^9$ is selected from divalent linear or branched $C_1$-$C_{10}$ alkane linking group, and for Formula (VI), $R^{10}$ is selected from divalent linear or branched $C_1$-$C_{10}$ alkane linking group, and $R^{11}$ is selected from fluorine, linear or branched fluorinated $C_1$-$C_{10}$ alkyl, or linear or branched perfluorinated $C_1$-$C_{10}$ alkyl.

Clause 22: The electrochromic composition of clause 20 or 21, wherein said cathodic component having cationic charge and said anodic component anion, selected from at least one anodic component anion represented by Formula (V) or Formula (VI), together have a net neutral charge.

Clause 23: The electrochromic composition of clause 20 or clause 21, wherein said anodic component further comprises a counter-cation.

Clause 24: The electrochromic composition of clause 23, wherein each counter-cation is independently selected from optionally substituted nitrogen-containing aliphatic heterocycle ammonium cations, optionally substituted nitrogen-containing aromatic heterocycle ammonium cations, tetrasubstituted ammonium cations, or combinations thereof.

Clause 25: The electrochromic composition of clause 23 or clause 24, wherein each counter-cation is independently selected from tetrasubstituted ammonium cations represented by the following Formula (C), Formula (C)

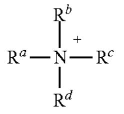

wherein $R^a$, $R^b$, $R^c$, and $R^d$ are each independently selected from linear or branched alkyl, unsubstituted cycloalkyl, substituted cycloalkyl, unsubstituted aryl, and substituted aryl.

Clause 26: The electrochromic composition of clause 25, wherein $R^a$, $R^b$, $R^c$, and $R^d$ are each independently selected from linear or branched $C_1$-$C_{10}$ alkyl, unsubstituted $C_3$-$C_7$ cycloalkyl, substituted $C_3$-$C_7$ cycloalkyl, unsubstituted phenyl, or substituted phenyl.

Clause 27: The electrochromic composition of clause 25 or clause 26, wherein $R^a$, $R^b$, $R^c$, and $R^d$ are each independently selected from linear or branched $C_1$-$C_{10}$ alkyl.

Clause 28: The electrochromic composition of any one of clauses 23, 24, 25, 26, or 27, wherein each counter-cation is independently selected from tetra(linear or branched alkyl) ammonium cation.

Clause 29: The electrochromic composition of any one of clauses 23, 24, 25, 26, 27, or 28, wherein each counter-cation is independently selected from tetra(linear or branched $C_1$-$C_{10}$ alkyl)ammonium cation.

Clause 30: The electrochromic composition of any one of clauses 18, 19, 20, 21, 23, 24, 25, 26, 27, 28, or 29, wherein said cathodic component further comprises counter-anions, wherein each counter-anion of the cathodic component is selected from the group consisting of $BF_4^-$, $PF_6^-$, $ClO_4^-$, $CF_3SO_3^-$, $(CF_3SO_2)_2N^-$, $(CF_3SO_2)_3C^-$, or $B(phenyl)_4^-$.

Clause 31: The electrochromic composition of any one of clauses 18, 19, 20, 21, 22, 23, 24, 25, 26, 27, 28, 29, or 30, wherein said electrolyte is present and comprises, at least one electrolyte anion, wherein each electrolyte anion is independently selected from bis(perfluoro(linear or branched $C_1$-$C_6$ alkylsulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, or 1-(linear or branched $C_1$-$C_6$ alkyl)-1-(linear or branched $C_1$-$C_6$ alkyl)piperidinium.

Clause 32: The electrochromic composition of any one of clauses 18, 19, 20, 21, 22, 23, 24, 25, 26, 27, 28, 29, 30, or 31, wherein said polymer thickener comprises a polymer, wherein said polymer comprises at least one of poly((meth) acrylonitrile), poly(vinylidene fluoride), poly(vinylidene fluoride-co-perfluoro(linear or branched $C_1$-$C_6$ alkylene)), poly((linear or branched $C_1$-$C_8$ alkyl)(meth)acrylate), or poly(diallyldimethylammonium $X^-$), wherein each $X^-$ independently is an anion represented by the following Formula (A), (A)

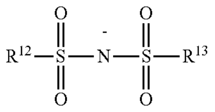

wherein $R^{12}$ and $R^{13}$ are each independently selected from fluorine, linear or branched fluorinated alkyl (or linear or branched fluorinated $C_1$-$C_{10}$ alkyl; or linear or branched fluorinated $C_1$-$C_8$ alkyl; or linear or branched fluorinated $C_1$-$C_5$ alkyl), or linear or branched perfluorinated alkyl (or linear or branched perfluorinated $C_1$-$C_{10}$ alkyl; or linear or branched perfluorinated $C_1$-$C_8$ alkyl; or linear or branched perfluorinated $C_1$-$C_5$ alkyl).

Clause 33: The electrochromic composition of any one of clauses 18, 19, 20, 21, 22, 23, 24, 25, 26, 27, 28, 29, 30, 31, or 32, wherein said polymer thickener comprises a polymer, wherein said polymer comprises poly(diallyldimethylammonium $X^-$), wherein each $X^-$ independently is an anion represented by the following Formula (A), (A)

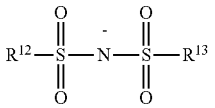

wherein $R^{12}$ and $R^{13}$ are each independently selected from fluorine, linear or branched fluorinated alkyl (or linear or branched fluorinated $C_1$-$C_{10}$ alkyl; or linear or branched fluorinated $C_1$-$C_8$ alkyl; or linear or branched fluorinated $C_1$-$C_5$ alkyl), or linear or branched perfluorinated alkyl (or linear or branched perfluorinated $C_1$-$C_{10}$ alkyl; or linear or branched perfluorinated $C_1$-$C_8$ alkyl; or linear or branched perfluorinated $C_1$-$C_5$ alkyl).

Clause 34: The electrochromic composition of any one of clauses 18, 19, 20, 21, 22, 23, 24, 25, 26, 27, 28, 29, 30, 31, 32, or 33, wherein said solvent comprises at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides.

The present invention is more particularly described in the following examples, which are intended as illustrative only, since numerous modifications and variations therein will be apparent to those skilled in the art.

EXAMPLES

In Part-1 of the examples there is described the synthesis of anodic components having an anion covalently bonded thereto, according to the present invention. In Part-2 there is described the synthesis of cathodic components according to the present invention. In Part-3 there is described the preparation of a poly(diallyldimethylammonium $X^-$) polymer according to the present invention. In Part-4, the preparation of an electrochromic device according to the present invention is described. In Part-5, the evaluation of the electrochromic device of Part-4 is described.

Part-1

Synthesis Example 1

With reference to Scheme-(1) below, there is provided a non-limiting description of the preparation of an anodic component having an anion covalently bonded thereto according to the present invention represented by Formula (V), where $R^9$ is a divalent n-propane linking group.

Into an oven dried 3-neck, 500 ml round bottomed flask with magnetic stirring was added 200 mL of dimethylformamide (DMF) and 10 g of (1) phenothiazine (50.2 mmol). The solution was stirred while being purge with nitrogen for 1 hour. To the reaction mixture was added 2.4 g of 60% NaH (60 mmol). The solution was observed to turn deep red as bubbles were produced therefrom. After continuous mixing under nitrogen for one hour, the production of bubbles was observed to cease. While under a nitrogen sweep is 6.6 g of (2) 1,3-propanesultone (55.2 mmol) dissolved in 10 g of dry DMF, was added drop-wise to the contents of the flask. After completion of the addition of (2) 1,3-propanesultone, the reaction mixture was left to stir at room temperature for 18 hours under nitrogen.

The reaction was quenched by the addition of 100 mL of deionized (DI) water and the solvent was removed by the application of vacuum, after which an oily substance remained in the flask. To the oily substance was added 50 mL of ethyl acetate, which resulted in the formation of a precipitate that was collected by vacuum filtration. The precipitate was washed with cold ethyl acetate and dried overnight under vacuum at 60° C. to yield the desired product (3) sodium 3-(10H-phenothiazin-10-yl)-propane-1-sulfonate, as an off-white solid.

Scheme-(1)

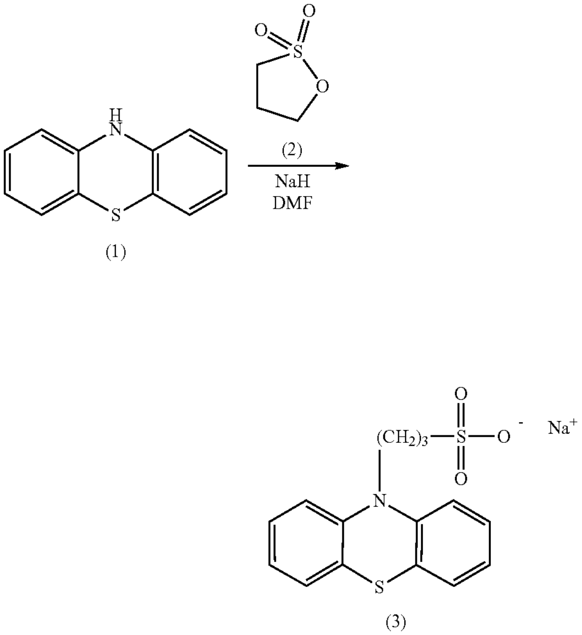

(1)

(3)

Part-1

Synthesis Example 2

With reference to Scheme-(2) below, there is provided a non-limiting description of the preparation of an anodic component having an anion covalently bonded thereto according to the present invention represented by Formula (VI), where $R^{10}$ is a divalent n-propane linking group, and $R^{11}$ is trifluoromethyl.

The (3) sodium 3-(10H-phenothiazin-10-yl)-propane-1-sulfonate was prepared in accordance with Synthesis Example 1. One gram (0.0029 mol) of (3) sodium 3-(10H-phenothiazin-10-yl)propane-1-sulfonate was fine ground with mortar and pestle, and then placed in a 100 ml round-bottom flask equipped with a magnetic stir bar and a reflux condenser with a $N_2$ sweep/blanket. Acetone in an amount of 20 ml and 40 mg of 18-crown-6 ether were added to the flask and the mixture was stirred vigorously for 15 minutes. The solution turned cloudy, but solid sodium salt (3) was observed to be present. (4) Cyanuric chloride (540 mg, 0.0029 mol, 1 equiv.) was added under vigorous stirring under $N_2$. The mixture was refluxed for 24 hours on an oil bath (at about 80° C.). The color of the solution turned orange and a fine precipitate formed. Large chunks of initial Na salt (3) were no longer observable. Thin layer chromatography (TLC) showed the presence of a single reaction product that turned pink upon exposure to short-wave (316 nm) UV in air, evidencing formation of (5) 3-(10H-phenothiazin-10-yl)-propane-1-sulfonyl chloride. The product (5) was fairly mobile in 50:50 EtOAc/Hexanes. The reaction mixture was cooled to room temperature and filtered through a thin layer of alumina. The solvent was removed under vacuum to give 1.25 g of orange-yellow glassy solid (5). The product (5) was dissolved in MeCN and the solids were filtered off. The filtrate was used in the next step without additional purification.

(6) Trifluoromethylsulfonamide (4.53 g, 0.0305 mol, 1.05 equiv.) and potassium carbonate (40 g, 0.29 mol, 10 equiv.) were placed in a 500 ml 3-neck flask equipped with a reflux condenser, magnetic stir bar and a fritted Schlenk funnel. Nitrogen feeds were attached to the condenser and the Schlenk funnel and secured with plastic clips. An intense nitrogen flux was used to flush the vessel for 15 seconds, and a septum was installed in the remaining neck. Anhydrous MeCN in an amount of 100 ml was added through the septum using a syringe. The mixture was vigorously stirred for 20 minutes, yielding a white hazy dispersion. To the crude (5) 3-(10H-phenothiazin-10-yl)propane-1-sulfonyl chloride (9.84 g, 0.029 mol) (filtrate of the preceding step) was added 50 ml dry MeCN under nitrogen flux, and the resulting solution was transferred to the fritted Schlenk funnel. The Schlenk funnel was purged with nitrogen and plugged with a stopper secured with a clip. The solution of MeCN and (5) 3-(10H-phenothiazin-10-yl)propane-1-sulfonyl chloride was added dropwise to the 3-neck flask over a period of one hour at room temperature. The contents of the 3-neck flask were refluxed for 24 hours. Formation of bulky precipitate was observed. The precipitate was filtered off and the resulting solution was concentrated under vacuum. The residue was recrystallized from water to yield the product (7) potassium 3-(10H-phenothiazin-10-yl)propane-1-triflimide, in the form of brown needles.

Scheme-(2)

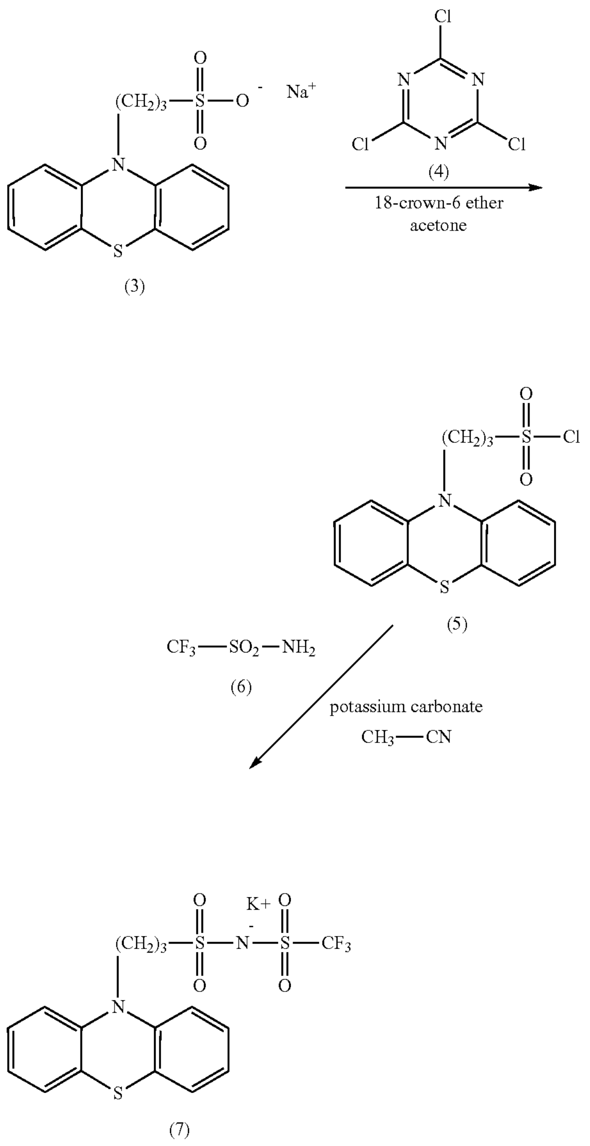

Part-2

Synthesis Example-3

With reference to Scheme-(3) below, there is provided a non-limiting description of the preparation of a cathodic component according to the present invention represented by Formula (I), where $R^1$ and $R^2$ are each represented by Formula (III), where $R^6$ in each case is $—CH_2CH_2CH_2—$.

In a suitably sized round bottom flask, 2 g of 4,4'-bipyridine (13) was dissolved in 50 ml of dry MeCN, followed by the addition of 3.28 g of 1,3-propanesultone (14) solution in MeCN. The contents of the flask were subjected to reflux overnight, followed by cooling to ambient room temperature. The resulting precipitate was collected and washed twice with MeCN to yield 4.96 g of 3,3'-([4,4'-bipyridinium]-1,1'-diyl)bis(propane-1-sulfonate) (15).

Scheme-(3)

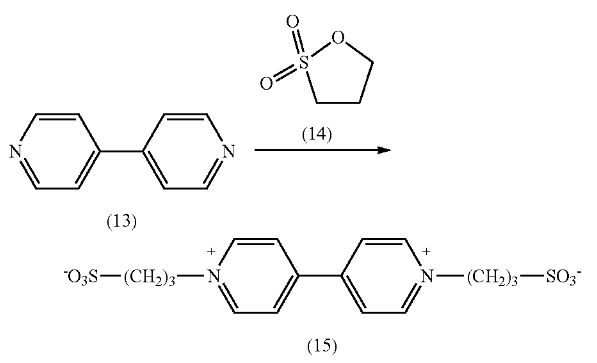

(13) (14) (15)

Part-2

Synthesis Example-4

With reference to Scheme-(4) below, there is provided a non-limiting description of the preparation of a cathodic component according to the present invention represented by Formula (I), where $R^1$ is N-triflylpropane-1-sulfonamide, $R^2$ is phenyl, and the counter-anion is bis(trifluoromethane) sulfonimide. To an Erlenmeyer flask equipped with a magnetic stirrer was added 4,4'-bipyridine (13) (20.3 g) and 1-chloro-2,4-dinitrobenzene (20) (15.6 g). Next, acetone was added (100 ml) and a reflux condenser was connected. The reaction mixture was refluxed under stirring for 24 hours. After cooling to room temperature, the mixture was filtered, and greenish solid was washed with hexane 3 times. Drying of the resulting solid with air gave 1-(2,4-dinitrophenyl)-4,4' bipyridinium chloride (22) with 57-67% yield (20.5-24.0 g).

To an Erlenmeyer flask equipped with a magnetic stirrer was added 5 g of (22) and ethanol (100 ml). Next, aniline (24) (3.5 ml) was added under stirring. A reflux condenser was connected and the reaction mixture was refluxed for 2 hours. The mixture was cooled to room temperature and solvent was removed on rotary evaporator. Water (200 ml) was added to the residue and the mixture was stirred at room temperature for 30 min. The mixture was filtered, and the solution was evaporated on rotary evaporator to give a yellow solid. This solid was washed with acetone 3 times and dried with air to give 1-phenyl-4,4'-bipyridinium chloride (26) with 95-99% yield (3.6-3.7 g).

To an Erlenmeyer flask equipped with a magnetic stirrer was added 1-phenyl-4,4-bipyridinium chloride (26) (1 g) and acetonitrile (80 ml). Then under stirring, a solution of potassium 3-chloro-N-triflylpropane-1-sulfonamide (28) (1 eq) in acetonitrile (20 ml) was added to the mixture. A reflux condenser was connected and the solution was refluxed under stirring for 4 hours. After cooling to room temperature, the mixture was filtered and the solid was washed with acetonitrile 2 times, then dried with air to give ((3-(1'-phenyl-[4,4'-bipyridine]-1,1'-diium-1-yl)propyl)sulfonyl) triflimide (30) with 79% yield (1.2 g).

To a glass beaker equipped with a magnetic stirrer was added, 1 g of (30) with water (50 ml). The mixture was stirred until full dissolution of starting reactant, then a solution of lithium bis(trifluoromethane)sulfonimide (32) (1.2 eq) in water (10 ml) was added dropwise under vigorous stirring at room temperature. The mixture was stirred for 30 min, then filtered. The white solid was washed with water 5 times and dried with air to give (34), referred to herein as PhVT, with 77% yield (1.2 g).

Scheme-(4)

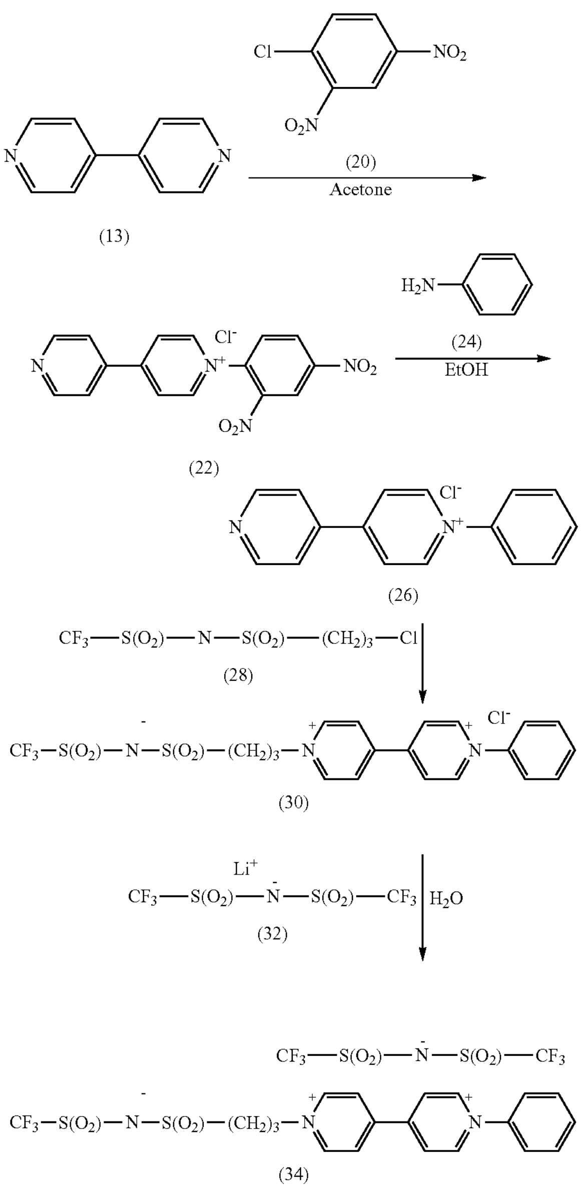

(13) (20) (22) (24) (26) (28) (30) (32) (34)

Part-3

With reference to Scheme-(5) below, there is provided a non-limiting description of the preparation of a poly(diallyldimethylammonium $X^-$) polymer according to the present invention, where with reference to Formula (A) as provided previously herein, $R^{12}$ and $R^{13}$ are each trifluoromethyl.

Into a double-neck, 2 liter round bottom flask fitted with a mechanical stirrer, was added 95 g of (11) lithium bis (trifluoromethane)sulfonimide and 300 ml of deionized water. The contents of the flask were then stirred at 500 rpm, and heated to and held at 80° C. While maintaining the contents of the flask at 80° C., 250 g of (10) poly(diallyldimethylammonium chloride) 20 wt % in water (obtained commercially from Sigma-Aldrich; having a reported Mw of 400 to 500 kDa) was added dropwise (310 mmol of chloride) over a period of 10 minutes. The contents of the flask were vigorously stirred at 800 rpm for 18 hours, followed by cooling to ambient room temperature, which resulted in the formation of a precipitate. The precipitate was collected by vacuum filtration, and washed several times with deionized water.

To a double-neck, 2 liter round bottom flask fitted with a mechanical stirrer, was added the collected and washed precipitate, 500 ml deionized water, and 10 g of (11) lithium bis(trifluoromethane)sulfonimide. With stirring at 800 rpm, the contents of the flask were heated to and held at 80° C. for 18 hours, followed by cooling to ambient room temperature, which resulted in the formation of a precipitate. The precipitate was collected by vacuum filtration and washed several times with deionized water, followed by several washings with methanol. The washed precipitate was collected and placed in a cellulose thimble, and Soxhlet extraction was conducted with methanol for 24 hours. The solvent was switched to acetone to collect the desired fraction. The solvent was removed under vacuum, and the resulting powder was dried under vacuum, which resulted in 110.9 g of (12) poly((diallyldimethylammonium bis(trifluoromethane) sulfonimide)), at a yield of approximately 88%.

Scheme-(5)

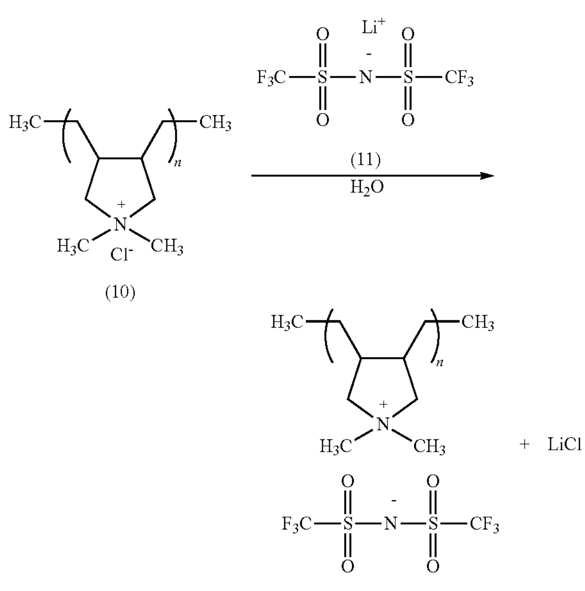

(10) (11) (12)

Part-4

An electrochromic device according to the present invention was prepared in accordance with the following procedure. An initial solution was prepared with magnetic stirring of the following: sulfolane (5 g); 1-ethyl-3-methylimidazolium bis(trifluoromethane)sulfonimide (EMIM-TFSI) (1 g); potassium 3-(10H-phenothiazin-10-yl)-N-((trifluoromethyl) sulfonyl)propane-1-sulfonamide (PTTK) (100 mg); and PhVT (see (34) of Scheme-4) (100 mg). To the initial solution was added 5 g of poly((diallyldimethylammonium bis(trifluoromethane)sulfonimide)) (PDADMA-TFSI), and then the combination was subjected to vigorous stirring with heat to form a thick solution. While hot, a volumetrically dosed portion of this solution was drop cast onto a fluorine-doped tin oxide (FTO)-glass electrode (3"×4"; 7.62 cm×10.16 cm) that had copper tape wrapped over the edge, which was covered with insulating polyimide. A prefabricated thermoplastic gasket of 0.5" (1.27 cm) in width and 400 microns in thickness was added, which surrounded the active area. A second fluorine-doped tin oxide (FTO)-glass electrode was positioned over of the electrochromic layer. The stack was subjected to vacuum lamination at 140° C. for 15 minutes to fully melt and seal the gasket. After cooling, the so formed electrochromic device was removed from the vacuum lamination device.

Part-5

Figure 2:
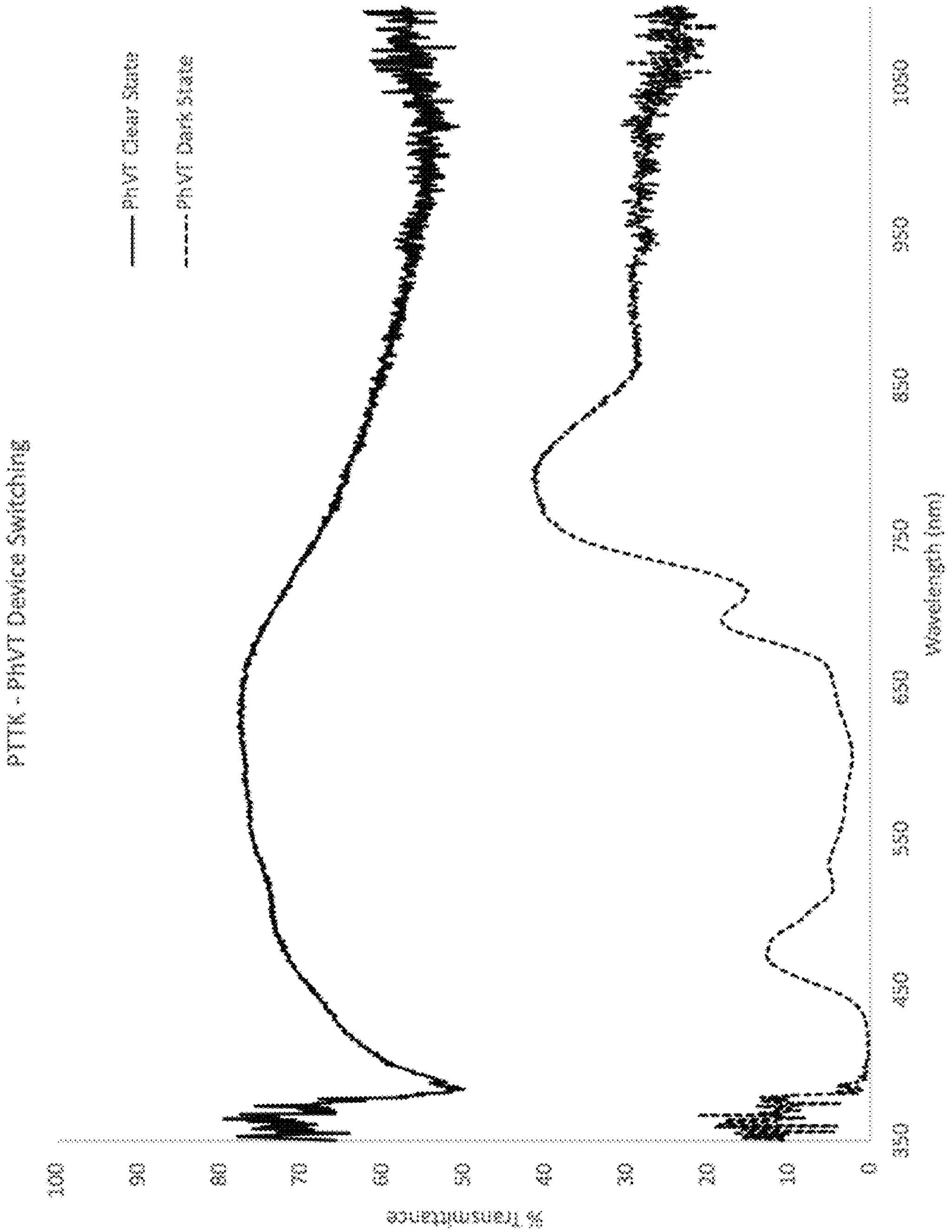
FIG. 2 is a graphical representation of plots of % transmission vs. wavelength obtained from an electrochromic device according to the present invention in the activated (dark) and unactivated (clear) states, as described in the Examiners herein.

Plots of % Transmission vs. Wavelength (nm) of the electrochromic device of Part-4 in the clear/unactivated state and the dark/activated state (in each case at room temperature) are depicted in FIG. 2 of the drawings. With reference to FIG. 2, the electrochromic device according to the present invention provides a significant and desirable level of darkening (i.e., reduced visual light transmission) when activated, as compared to the clear/unactivated state thereof. In FIG. 2, the electrochromic device of Part-4 is referred to as a “PTTK-PhVT Device” followed by the term “Switching” with regard to the clear state and dark state plots. With additional reference to FIG. 2: the plot of % Transmission vs. Wavelength in the clear/unactivated state is labeled “PhVT Clear State”; and the plot of % Transmission vs. Wavelength in the darkened/activated state is labeled “PhVT Dark State.”

The present invention has been described with reference to specific details of particular embodiments thereof. It is not intended that such details be regarded as limitations upon the scope of the invention except insofar as to the extent that they are included in the accompanying claims.

What is claimed is:

1. An electrochromic device comprising:

(a) a first substrate having a surface comprising a first transparent electrode layer;

(b) a second substrate having a surface comprising a second transparent conductive electrode layer, wherein said first transparent electrode layer and said second transparent electrode layer are in opposing spaced opposition; and (c) an electrochromic layer interposed between said first transparent electrically conductive electrode layer and said second transparent electrically conductive electrode layer, wherein said electrochromic layer comprises, (i) a cathodic component, (ii) an anodic component, (iii) an optional electrolyte, and (iv) a polymer matrix, wherein said cathodic component comprises a cathodic component having cationic charge selected from at least one of a 1,1'-disubstituted-4,4'-dipyridinium cation represented by the following Formula (I), or a 1,1-(alkane-alpha, omega-diyl)-bis-(1'-substituted-4,4'-dipyridinium) cation represented by the following Formula (II), (I)

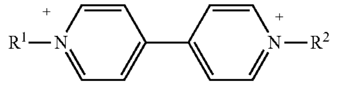

(II)

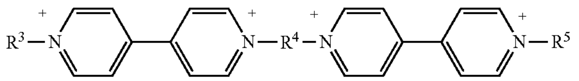

wherein for Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by the following Formula (III), $—R^6—SO_3^-$ (III), and a group represented by the following Formula (IV), (IV)

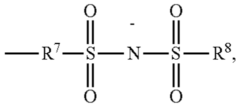

wherein for Formula (III) and Formula (IV), $R^6$ and $R^7$ are in each case independently selected from divalent linear or branched alkane linking group, and for Formula (IV), $R^8$ is selected from fluorine, linear or branched fluorinated alkyl, or linear or branched perfluorinated alkyl, and for Formula (II), $R^4$ is selected from divalent linear or branched alkane linking group, provided that for Formula (I), at least one of $R^1$ and $R^2$ is independently selected from said group represented by Formula (IV), and provided that for Formula (II), at least one of $R^3$ and $R^5$ is independently selected from said group represented by Formula (IV).

2. The electrochromic device of claim 1, wherein for Formula (I) and Formula (II), $R^1$, $R^2$, $R^3$, and $R^5$ are in each case independently selected from linear or branched $C_1$-$C_{10}$ alkyl, unsubstituted $C_3$-$C_7$ cycloalkyl, substituted $C_3$-$C_7$ cycloalkyl, unsubstituted phenyl, substituted phenyl, said group represented by Formula (III), and said group represented by Formula (IV), wherein for Formula (III) and Formula (IV), $R^6$ and $R^7$ are in each case independently selected from divalent linear or branched $C_1$-$C_{10}$ alkane linking group, and for Formula (IV), $R^8$ is selected from fluorine, linear or branched fluorinated $C_1$-$C_{10}$ alkyl, or linear or branched perfluorinated $C_1$-$C_{10}$ alkyl, and for Formula (II), $R^4$ is selected from divalent linear or branched $C_1$-$C_{10}$ alkane linking group.

3. The electrochromic device of claim 1, wherein said anodic component comprises an anodic component anion selected from at least one anodic component anion represented by the following Formula (V) or Formula (VI), (V)

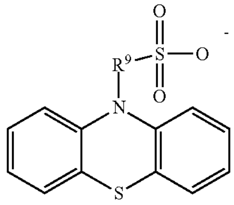

(VI)

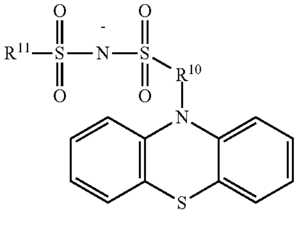

wherein for Formula (V), $R^9$ is selected from divalent linear or branched alkane linking group, and for Formula (VI), $R^{10}$ is selected from divalent linear or branched alkane linking group, and $R^{11}$ is selected from fluorine, linear or branched fluorinated alkyl, or linear or branched perfluorinated alkyl.

4. The electrochromic device of claim 3, wherein for Formula (V), $R^9$ is selected from divalent linear or branched $C_1$-$C_{10}$ alkane linking group, and for Formula (VI), $R^{10}$ is selected from divalent linear or branched $C_1$-$C_{10}$ alkane linking group, and $R^{11}$ is selected from fluorine, linear or branched fluorinated $C_1$-$C_{10}$ alkyl, or linear or branched perfluorinated $C_1$-$C_{10}$ alkyl.

5. The electrochromic device of claim 3, wherein said cathodic component having cationic charge and said anodic component anion together have a net neutral charge.

6. The electrochromic device of claim 3, wherein said anodic component further comprises a counter-cation.

7. The electrochromic device of claim 6, wherein each counter-cation is independently selected from tetra(linear or branched alkyl)ammonium cation.

8. The electrochromic device of claim 1, wherein said cathodic component further comprises counter-anions, wherein each counter-anion of the cathodic component is selected from the group consisting of $BF_4^-$, $PF_6^-$, $ClO_4^-$, $CF_3SO_3^-$, $(CF_3SO_2)_2N^-$, $(CF_3SO_2)_3C^-$, and $B(phenyl)_4^-$.

9. The electrochromic device of claim 1, wherein said electrolyte is present and comprises, at least one electrolyte anion, wherein each electrolyte anion is independently selected from bis(perfluoro(linear or branched $C_1$-$C_6$ alkylsulfonyl)imide, and at least one electrolyte cation, wherein each electrolyte cation is independently selected from 1-(linear or branched $C_1$-$C_6$ alkyl)-3-(linear or branched $C_1$-$C_6$ alkyl) imidazolium, 1-(linear or branched $C_1$-$C_6$ alkyl)-1-(linear or branched $C_1$-$C_6$ alkyl)piperidinium, tetra (linear or branched $C_1$-$C_6$ alkyl)phosphonium, tri($C_5$-$C_8$ cycloalkyl)-(linear or branched $C_1$-$C_6$ alkyl) phosphonium, tetra(linear or branched $C_1$-$C_6$) ammonium, and tri($C_5$-$C_8$ cycloalkyl)-(linear or branched $C_1$-$C_6$ alkyl)ammonium.

10. The electrochromic device of claim 1, wherein said polymer matrix comprises a polymer, wherein said polymer comprises at least one of poly((meth)acrylonitrile), poly (vinylidene fluoride), poly(vinylidene fluoride-co-perfluoro (linear or branched $C_1$-$C_6$ alkylene)), poly((linear or branched $C_1$-$C_8$ alkyl)(meth)acrylate), or poly(diallyldimethylammonium $X^-$), wherein each $X^-$ independently is an anion represented by the following Formula (A), (A)

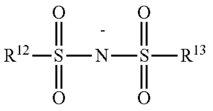

wherein $R^{12}$ and $R^{13}$ are each independently selected from fluorine, linear or branched fluorinated alkyl, or linear or branched perfluorinated alkyl.

11. The electrochromic device of claim 1, wherein said polymer matrix comprises a polymer, wherein said polymer comprises poly(diallyldimethylammonium $X^-$), wherein each $X^-$ independently is an anion represented by the following Formula (A), (A)

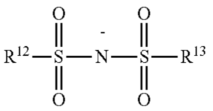

wherein $R^{12}$ and $R^{13}$ are each independently selected from fluorine, linear or branched fluorinated alkyl, or linear or branched perfluorinated alkyl.

12. An electrochromic composition comprising, (i) a cathodic component, (ii) an anodic component, (iii) an optional electrolyte, (iv) a polymeric thickener, and (v) a solvent, wherein said cathodic component comprises a cathodic component having cationic charge selected from at least one of a 1,1'-disubstituted-4,4'-dipyridinium cation represented by the following Formula (I), or a 1,1-(alkane-alpha, omega-diyl)-bis-(1'-substituted-4,4'-dipyridinium) cation represented by the following Formula (II), (I)

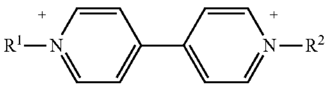

(II)

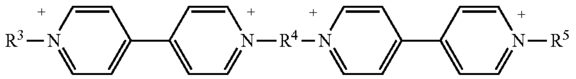

wherein for Formula (I) and Formula (II), $R^1$, $R^2$, $R^3$, and $R^5$ are in each case independently selected from linear or branched alkyl, unsubstituted cycloalkyl, substituted cycloalkyl, unsubstituted aryl, substituted aryl, a group represented by the following Formula (III), $—R^6—SO_3^-$ (III), and a group represented by the following Formula (IV), (IV)

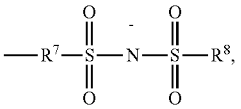

wherein for Formula (III) and Formula (IV), $R^6$ and $R^7$ are in each case independently selected from divalent linear or branched alkane linking group, and for Formula (IV), $R^8$ is selected from fluorine, linear or branched fluorinated alkyl, or linear or branched perfluorinated alkyl, and for Formula (II), $R^4$ is selected from divalent linear or branched alkane linking group, provided that for Formula (I), at least one of $R^1$ and $R^2$ is independently selected from said group represented by Formula (IV), and provided that for Formula (II), at least one of $R^3$ and $R^5$ is independently selected from said group represented by Formula (IV).

13. The electrochromic composition of claim 12, wherein for Formula (I) and Formula (II), $R^1$, $R^2$, $R^3$, and $R^5$ are in each case independently selected from linear or branched $C_1$-$C_{10}$ alkyl, unsubstituted $C_3$-$C_7$ cycloalkyl, substituted $C_3$-$C_7$ cycloalkyl, unsubstituted phenyl, and substituted phenyl, said group represented by Formula (III), and said group represented by Formula (IV), wherein for Formula (III) and Formula (IV), $R^6$ and $R^7$ are in each case independently selected from divalent linear or branched $C_1$-$C_{10}$ alkane linking group, and for Formula (IV), $R^8$ is selected from fluorine, linear or branched fluorinated $C_1$-$C_{10}$ alkyl, or linear or branched perfluorinated $C_1$-$C_{10}$ alkyl, and for Formula (II), $R^4$ is selected from divalent linear or branched $C_1$-$C_{10}$ alkane linking group.

14. The electrochromic composition of claim 12, wherein said anodic component comprises an anodic component anion selected from at least one anodic component anion represented by the following Formula (V) or Formula (VI), (V)

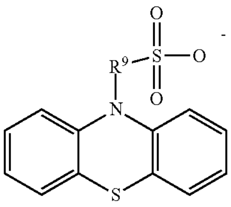

(VI)

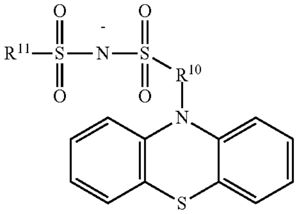

wherein for Formula (V), $R^9$ is selected from divalent linear or branched alkane linking group, and for Formula (VI), $R^{10}$ is selected from divalent linear or branched alkane linking group, and $R^{11}$ is selected from fluorine, linear or branched fluorinated alkyl, or linear or branched perfluorinated alkyl.

15. The electrochromic composition of claim 14, wherein for Formula (V), $R^9$ is selected from divalent linear or branched $C_1$-$C_{10}$ alkane linking group, and for Formula (VI), $R^{10}$ is selected from divalent linear or branched $C_1$-$C_{10}$ alkane linking group, and $R^{11}$ is selected from fluorine, linear or branched fluorinated $C_1$-$C_{10}$ alkyl, or linear or branched perfluorinated $C_1$-$C_{10}$ alkyl.

16. The electrochromic composition of claim 14, wherein said cathodic component having cationic charge and said anodic component anion together have a net neutral charge.

17. The electrochromic composition of claim 14, wherein said anodic component further comprises a counter-cation.

18. The electrochromic composition of claim 17, wherein each counter-cation is independently selected from tetra (linear or branched alkyl) ammonium cation.

19. The electrochromic composition of claim 12, wherein said cathodic component further comprises counter-anions, wherein each counter-anion of the cathodic component is selected from the group consisting of $BF_4^-$, $PF_6^-$, $ClO_4^-$, $CF_3SO_3^-$, $(CF_3SO_2)_2N^-$, $(CF_3SO_2)_3C^-$, and $B(phenyl)_4^-$.

20. The electrochromic composition of claim 12, wherein said electrolyte is present and comprises, at least one electrolyte anion, wherein each electrolyte anion is independently selected from bis(perfluoro(linear or branched $C_1$-$C_6$ alkylsulfonyl)imide, and at least one electrolyte cation, wherein each electrolyte cation is independently selected from 1-(linear or branched $C_1$-$C_6$ alkyl)-3-(linear or branched $C_1$-$C_6$ alkyl) imidazolium, 1-(linear or branched $C_1$-$C_6$ alkyl)-1-(linear or branched $C_1$-$C_6$ alkyl)piperidinium, tetra (linear or branched $C_1$-$C_6$ alkyl)phosphonium, tri($C_5$-$C_8$ cycloalkyl)-(linear or branched $C_1$-$C_6$ alkyl) phosphonium, tetra(linear or branched $C_1$-$C_6$) ammonium, and tri($C_5$-$C_8$ cycloalkyl)-(linear or branched $C_1$-$C_6$ alkyl)ammonium.

21. The electrochromic composition of claim 12, wherein said polymer thickener comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), poly((linear or branched $C_1$-$C_8$ alkyl)(meth)acrylate), or poly(diallyldimethylammonium $X^-$), wherein each $X^-$ independently is an anion represented by the following Formula (A), (A)

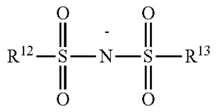

wherein $R^{12}$ and $R^{13}$ are each independently selected from fluorine, linear or branched fluorinated alkyl, or linear or branched perfluorinated alkyl.

22. The electrochromic composition of claim 12, wherein said polymer thickener comprises a polymer, wherein said polymer comprises poly(diallyldimethylammonium $X^-$), wherein each $X^-$ independently is an anion represented by the following Formula (A), (A)

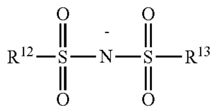

wherein $R^{12}$ and $R^{13}$ are each independently selected from fluorine, linear or branched fluorinated alkyl, or linear or branched perfluorinated alkyl.

23. The electrochromic composition of claim 12, wherein said solvent comprises at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$) acetamides.

* * * * *